(12) United States Patent
Kinomoto et al.

(10) Patent No.: US 12,667,344 B2
(45) Date of Patent: **\*Jun. 30, 2026**

(54) ULTRASOUND ENDOSCOPE FOR PREVENTING A NON-COAXIAL CABLE FROM BEING DISCONNECTED AND IMPROVING A DEGREE OF FREEDOM OF WIRING

(71) Applicant: FUJIFILM Corporation, Tokyo (JP)

(72) Inventors: Noboru Kinomoto, Ashigarakami-gun (JP); Yasuhiko Morimoto, Ashigarakami-gun (JP)

(73) Assignee: FUJIFILM Corporation, Tokyo (JP)

( \* ) Notice: Subject to any disclaimer, the term of this patent is extended or adjusted under 35 U.S.C. 154(b) by 0 days.

This patent is subject to a terminal disclaimer.

(21) Appl. No.: 19/073,960

(22) Filed: Mar. 7, 2025

(65) Prior Publication Data

US 2025/0204894 A1 Jun. 26, 2025

Related U.S. Application Data

(63) Continuation of application No. 17/381,376, filed on Jul. 21, 2021, now Pat. No. 12,274,585.

(30) Foreign Application Priority Data

Sep. 8, 2020 (JP) ................................. 2020-150291

(51) Int. Cl.
*A61B 8/00* (2006.01)
*A61B 8/12* (2006.01)
(52) U.S. Cl.
CPC .................. *A61B 8/56* (2013.01); *A61B 8/12* (2013.01); *A61B 8/4488* (2013.01)

(58) Field of Classification Search
CPC ........... A61B 8/56; A61B 8/12; A61B 8/4488; A61B 1/00091; A61B 1/00096;
(Continued)

(56) References Cited

U.S. PATENT DOCUMENTS

| | | |
|---|---|---|
| 8,517,949 B2 | 8/2013 | Hiraoka |
| 10,201,311 B2 | 2/2019 | Chou et al. |

(Continued)

FOREIGN PATENT DOCUMENTS

| | | |
|---|---|---|
| JP | 2001-104311 A | 4/2001 |
| JP | 2010-12068 A | 1/2010 |

(Continued)

OTHER PUBLICATIONS

Advisory Action issued in U.S. Appl. No. 17/381,376, filed Jun. 6, 2024.

(Continued)

*Primary Examiner* — Serkan Akar
(74) *Attorney, Agent, or Firm* — Birch, Stewart, Kolasch & Birch, LLP

(57) ABSTRACT

Provided is an ultrasound endoscope capable of preventing a non-coaxial cable from being disconnected and improving a degree of freedom of wirings.
An ultrasound endoscope includes a first cable that electrically connects a substrate electrically connected to a plurality of ultrasound transducers and a relay substrate, the first cable includes a plurality of first non-coaxial cables, a plurality of first electrical bonded portions are formed by signal wires of a first cable bundle of the first non-coaxial cables and electrode pads of the substrate, a plurality of second electrical bonded portions are formed by the signal wires of the first cable bundle and first cable-side electrode pads of the relay substrate, and a plurality of first electrical (Continued)

bonded portions and a plurality of second electrical bonded portions are collectively disposed for each first cable bundle.

10 Claims, 15 Drawing Sheets

(58) Field of Classification Search
CPC ....... A61B 1/00098; A61B 1/018; A61B 1/05; A61B 8/4281; A61B 8/4416; A61B 8/4483; A61B 8/4494; A61B 8/4444; A61B 8/445; A61B 8/44
See application file for complete search history.

(56) References Cited

U.S. PATENT DOCUMENTS

| | | | |
|---|---|---|---|
| 10,741,306 B2 | 8/2020 | Kobayashi et al. | |
| 2013/0072801 A1 | 3/2013 | Hiraoka | |
| 2013/0333917 A1 | 12/2013 | Tanabe | |
| 2013/0341065 A1 | 12/2013 | Sato et al. | |
| 2015/0011891 A1 | 1/2015 | Yamada | |
| 2018/0247740 A1 | 8/2018 | Khamphilavong et al. | |
| 2020/0205777 A1 | 7/2020 | Kumata | |
| 2020/0297307 A1 | 9/2020 | Khalaj et al. | |

FOREIGN PATENT DOCUMENTS

| | | | |
|---|---|---|---|
| JP | 2013-206617 A | 10/2013 | |
| JP | 2014-29846 A | 2/2014 | |
| JP | 2017-73662 A | 4/2017 | |
| JP | 2019-54962 A | 4/2019 | |
| WO | WO 2012/120993 A1 | 9/2012 | |
| WO | WO 2012/157354 A1 | 11/2012 | |

OTHER PUBLICATIONS

Advisory Action issued in U.S. Appl. No. 17/381,376, filed May 25, 2023.

Japanese Office Action for corresponding Japanese Application No. 2020-150291, dated Mar. 27, 2023, with English translation.

Japanese Office Action for corresponding Japanese Application No. 2023-178881, dated Jun. 6, 2024, with an English translation.

Notice of Allowance issued in U.S. Appl. No. 17/381,376, filed Dec. 11, 2024.

Office Action Issued in U.S. Appl. No. 17/381,376, filed Aug. 16, 2022.

Office Action issued in U.S. Appl. No. 17/381,376, filed Feb. 1, 2023.

Office Action issued in U.S. Appl. No. 17/381,376, filed Feb. 22, 2024.

Office Action issued in U.S. Appl. No. 17/381,376, filed Sep. 22, 2023.

ULTRASOUND ENDOSCOPE FOR PREVENTING A NON-COAXIAL CABLE FROM BEING DISCONNECTED AND IMPROVING A DEGREE OF FREEDOM OF WIRING

CROSS-REFERENCE TO RELATED APPLICATIONS

The present application is a Continuation of U.S. application Ser. No. 17/381,376, filed Jul. 21, 2021, which application claims priority under 35 U.S.C § 119 to Japanese Patent Application No. 2020-150291 filed on Sep. 8, 2020. The above applications are hereby expressly incorporated by reference, in their entirety, into the present application.

BACKGROUND OF THE INVENTION

1. Field of the Invention

The present invention relates to an ultrasound endoscope.

2. Description of the Related Art

In recent years, an ultrasound endoscope that observes a state inside a body of a subject by irradiating the inside of the body with ultrasonic waves and receives reflected waves to capture video has been used in medical practice.

For example, as disclosed in JP2019-054962A, such an ultrasound endoscope comprises a distal end part that comprises piezoelectric elements configuring ultrasound transducers, a bending part and a flexible part connected to a proximal end of the distal end part, a plurality of coaxial cables that are inserted into the bending part and the flexible part, and a wiring substrate that electrically connects the piezoelectric elements and the coaxial cables.

SUMMARY OF THE INVENTION

Incidentally, a coaxial cable is formed by covering a shield layer and an outer coat the periphery of one signal wire coated for insulation. For this reason, the outside diameter of the coaxial cable increases, and the ultrasound endoscope is hardly reduced in diameter.

Accordingly, a case where an ultrasound endoscope is reduced in diameter by applying a non-coaxial cable instead of the coaxial cable is considered. However, the non-coaxial cable does not comprise the shield layer and the outer coat for each one signal wire. For this reason, there is a problem in that the non-coaxial cable is likely to be cut at the time of connection to a wiring substrate.

The non-coaxial cable is electrically bonded with a plurality of signal wires as one set, and accordingly, a degree of freedom of wirings in connection to the substrate is low. At the time of connection to a connector substrate on a proximal end side with the non-coaxial cable, in a case where an arrangement order of the signal wires of the non-coaxial cable is different from an arrangement order of electrode pads of the connector substrate, there is a problem in that electrical bonding is difficult.

The invention has been accomplished in view of such a situation, and an object of the invention is to provide an ultrasound endoscope capable of preventing a non-coaxial cable from being disconnected and improving a degree of freedom of wirings.

An ultrasound endoscope of a first aspect comprises an insertion part that includes a distal end part having an ultrasound transducer array in which a plurality of ultrasound transducers are arranged, a first cable that is inserted into the insertion part, a substrate that electrically connects the plurality of ultrasound transducers and the first cable, and a second cable that has a proximal end side electrically connected to a connector substrate on a proximal end side from the first cable. The first cable has a first non-coaxial cable that includes a first cable bundle consisting of a plurality of signal wires and a plurality of ground wires, and a first shield layer with which the first cable bundle is coated, and an outer coat with which a second cable bundle consisting of a plurality of the first non-coaxial cables is coated, the substrate includes a plurality of electrode pads connected to the plurality of ultrasound transducers, respectively, the electrode pads and the signal wires of the first cable bundles are electrically connected to form a plurality of first electrical bonded portions, the plurality of first electrical bonded portions are collectively disposed for each first cable bundle, a relay substrate that electrically connects a proximal end side of the first cable and a distal end side of the second cable is disposed, the relay substrate includes a plurality of first cable-side electrode pads corresponding to the signal wires included in the first cable bundles, the first cable-side electrode pads and the signal wires of the first cable bundles are connected to form a plurality of second electrical bonded portions, and the plurality of second electrical bonded portions are collectively disposed for each first cable bundle.

In an ultrasound endoscope of a second aspect, the second cable has a second non-coaxial cable that includes a third cable bundle consisting of a plurality of signal wires and a plurality of ground wires, and a second shield layer with which the third cable bundle is coated, and an outer coat with which a fourth cable bundle consisting of a plurality of the second non-coaxial cables is coated, the relay substrate includes a plurality of second cable-side electrode pads corresponding to the signal wires included in the third cable bundles of the second cable, the second cable-side electrode pads and the signal wires of the third cable bundles are connected to form a plurality of third electrical bonded portions, the plurality of third electrical bonded portions are collectively disposed for each third cable bundle, and the relay substrate electrically connects the plurality of second electrical bonded portions and the plurality of third electrical bonded portions in different arrangement orders, in a one-to-one correspondence relationship.

In an ultrasound endoscope of a third aspect, the connector substrate includes a plurality of connector electrode pads corresponding to the signal wires included in the third cable bundles of the second cable, the connector electrode pads and the signal wires included in the third cable bundles are connected to form a plurality of fourth electrical bonded portions, and the plurality of fourth electrical bonded portions are collectively disposed for each third cable bundle.

In an ultrasound endoscope of a fourth aspect, the second cable is configured by putting together a plurality of coaxial cables each having a signal wire.

In an ultrasound endoscope of a fifth aspect, the signal wires included in the second cable have a greater outside diameter, a longer outer peripheral length, or both a greater outside diameter and a longer outer peripheral length than the signal wires included in the first cables.

An ultrasound endoscope of a sixth aspect further comprises a fixing member that reinforces the relay substrate.

In an ultrasound endoscope of a seventh aspect, the fixing member is a metallic member, and the metallic member is electrically connected to the first shield layer of each first non-coaxial cable.

An ultrasound endoscope of an eighth aspect further comprises an insulation coating member with which the relay substrate is coated.

In an ultrasound endoscope of a ninth aspect, the relay substrate is disposed on a proximal end side from the distal end part in the insertion part.

An ultrasound endoscope of a tenth aspect further comprises an operating part that is connected to a proximal end side of the insertion part, and the relay substrate is disposed in the operating part.

With the ultrasound endoscope according to the aspects of the invention, it is possible to prevent a non-coaxial cable from being disconnected and to improve a degree of freedom of wirings.

BRIEF DESCRIPTION OF THE DRAWINGS

FIG. 3 is a cross-sectional view taken along the line III-III of FIG. 2.

FIG. 9 is a diagram showing a connection structure of the relay substrate and a second cable.

FIGS. 15A to 15C are diagrams showing insulation coating members that are provided in the relay substrate.

DESCRIPTION OF THE PREFERRED EMBODIMENTS

Hereinafter, a preferred embodiment of an ultrasound endoscope according to the invention will be described referring to the accompanying drawings.

Figure 1:
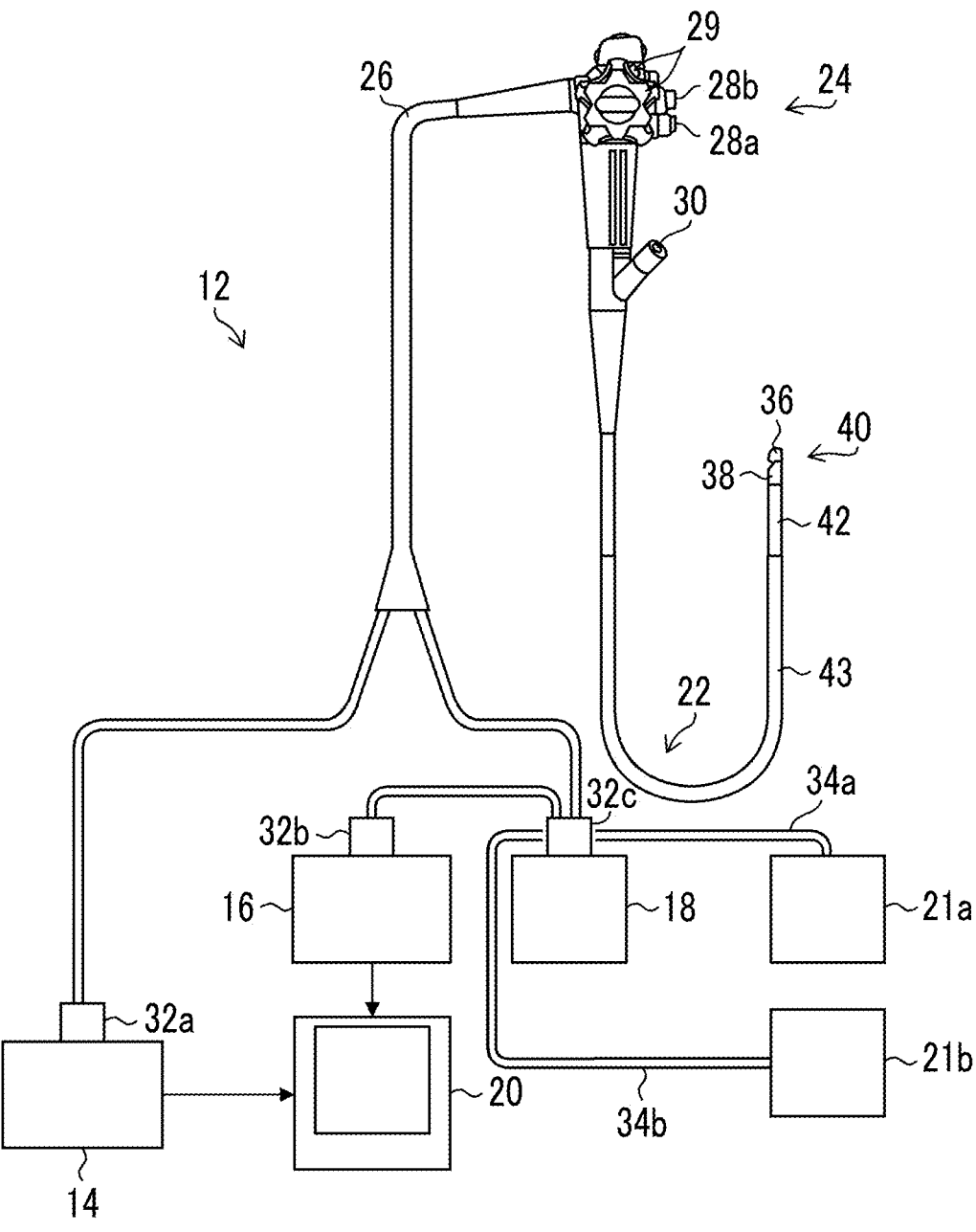
FIG. 1 is a schematic configuration diagram showing an example of the configuration of an ultrasonography system.

FIG. 1 is a schematic configuration diagram showing an example of an ultrasonography system 10 that uses an ultrasound endoscope 12 of an embodiment.

As shown in FIG. 1, the ultrasonography system 10 comprises an ultrasound endoscope 12, an ultrasound processor device 14 that generates an ultrasound image, an endoscope processor device 16 that generates an endoscope image, a light source device 18 that supplies illumination light, with which the inside of a body cavity is illuminated, to the ultrasound endoscope 12, and a monitor 20 that displays the ultrasound image and the endoscope image. The ultrasonography system 10 comprises a water supply tank 21a that stores cleaning water or the like, and a suction pump 21b that sucks aspirates inside the body cavity.

The ultrasound endoscope 12 has an insertion part 22 that is inserted into the body cavity of the subject, an operating part 24 that is consecutively provided in a proximal end portion of the insertion part 22 and is used by an operator to perform an operation, and a universal cord 26 that has one end connected to the operating part 24.

In the operating part 24, an air and water supply button 28a that opens and closes an air and water supply pipe line (not shown) from the water supply tank 21a, and a suction button 28b that opens and closes a suction pipe line (not shown) from the suction pump 21b are provided side by side. In the operating part 24, a pair of angle knobs 29 and 29 and a treatment tool insertion port 30 are provided.

In the other end portion of the universal cord 26, an ultrasound connector 32a that is connected to the ultrasound processor device 14, an endoscope connector 32b that is connected to the endoscope processor device 16, and a light source connector 32c that is connected to the light source device 18 are provided. The ultrasound endoscope 12 are attachably and detachably connected to the ultrasound processor device 14, the endoscope processor device 16, and the light source device 18 respectively through the connectors 32a, 32b, and 32c. The connector 32c comprises an air and water supply tube 34a that is connected to the water supply tank 21a, and a suction tube 34b that is connected to the suction pump 21b.

The insertion part 22 has, in order from a distal end side, a distal end part 40 having an ultrasound observation part 36 and an endoscope observation part 38, a bending part 42 that is consecutively provided on a proximal end side of the distal end part 40, and a flexible part 43 that couples a proximal end side of the bending part 42 and the distal end side of the operating part 24.

The bending part 42 is remotely bent and operated by rotationally moving and operating a pair of angle knobs 29 and 29 provided in the operating part 24. With this, the distal end part 40 can be directed in a desired direction.

The ultrasound processor device 14 generates and supplies an ultrasound signal for making an ultrasound transducer array 50 of an ultrasound transducer unit 46 (see FIG. 2) of the ultrasound observation part 36 described below generate an ultrasonic wave. The ultrasound processor device 14 receives and acquires an echo signal reflected from an observation target part irradiated with the ultrasonic wave, by the ultrasound transducer array 50 and executes various kinds of signal processing on the acquired echo signal to generate an ultrasound image that is displayed on the monitor 20.

The endoscope processor device 16 receives and acquires a captured image signal acquired from the observation target part illuminated with illumination light from the light source device 18 in the endoscope observation part 38 and execute various kinds of signal processing and image processing on the acquired image signal to generate an endoscope image that is displayed on the monitor 20.

The ultrasound processor device 14 and the endoscope processor device 16 are configured with two devices (computers) provided separately. Note that the invention is not limited thereto, and both the ultrasound processor device 14 and the endoscope processor device 16 may be configured with one device.

To image an observation target part inside a body cavity using the endoscope observation part 38 to acquire an image signal, the light source device 18 generates illumination light, such as white light including light of three primary colors of red light, green light, and blue light or light of a specific wavelength. Light propagates through a light guide (not shown) and the like in the ultrasound endoscope 12, and is emitted from the endoscope observation part 38, and the observation target part inside the body cavity is illuminated with light.

The monitor 20 receives video signals generated by the ultrasound processor device 14 and the endoscope processor device 16 and displays an ultrasound image and an endoscope image. In regard to the display of the ultrasound image and the endoscope image, only one image may be appropriately switched and displayed on the monitor 20 or both images may be displayed simultaneously.

In the embodiment, although the ultrasound image and the endoscope image are displayed on one monitor 20, a monitor for ultrasound image display and a monitor for endoscope image display may be provided separately. Alternatively, the ultrasound image and the endoscope image may be displayed in a display form other than the monitor 20, for example, in a form of being displayed on a display of a terminal carried with the operator.

Next, the configuration of the distal end part 40 will be described referring to FIGS. 2 to 4.

Figure 2:
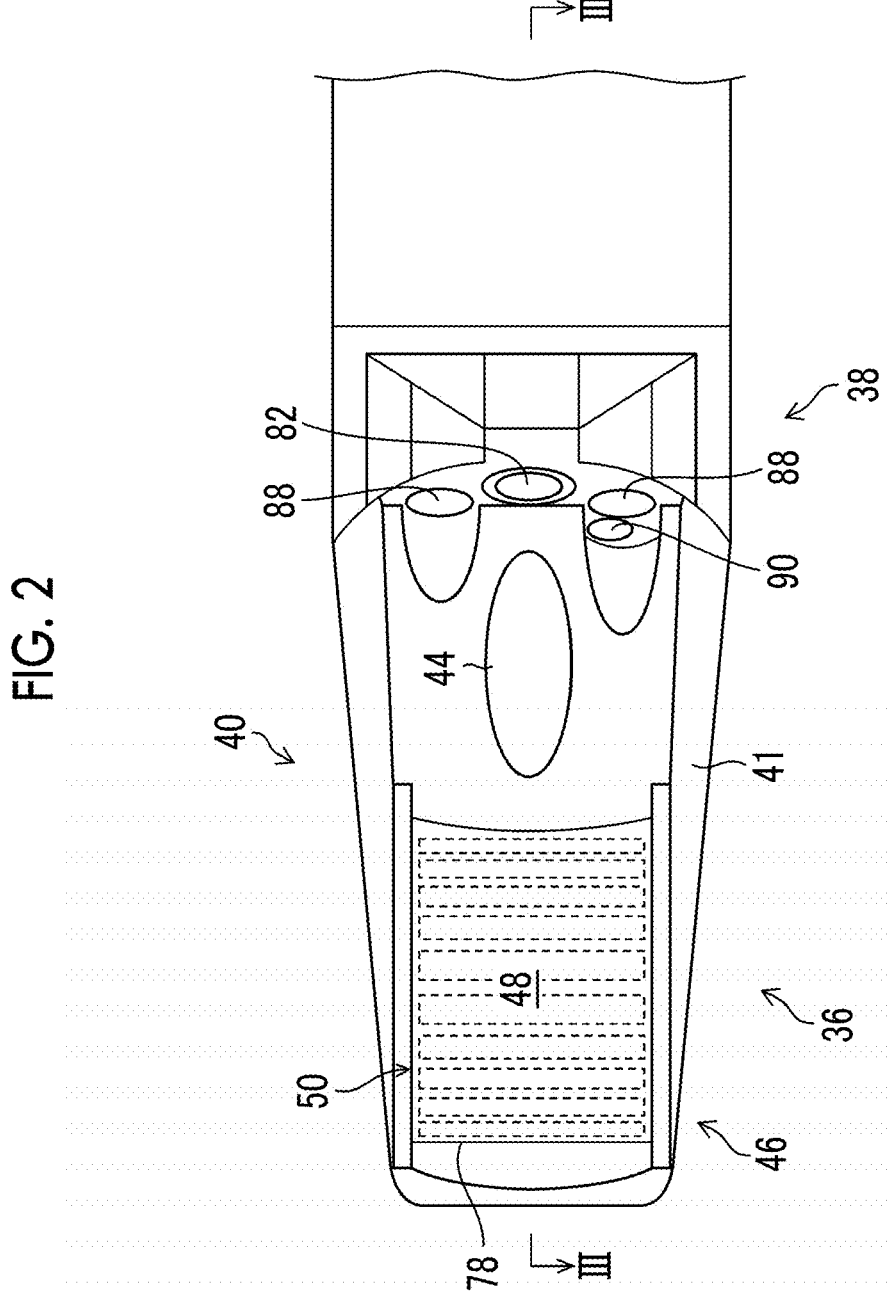
FIG. 2 is a partial enlarged plan view showing a distal end part of an ultrasound endoscope of FIG. 1 and the vicinity of the distal end part.

FIG. 2 is a partial enlarged plan view showing the distal end part 40 shown in FIG. 1 and the vicinity thereof the distal end part 40. FIG. 3 is a cross-sectional view taken along the line III-III shown in FIG. 2, and is a longitudinal sectional view of the distal end part 40 taken along a center line thereof in a longitudinal axis direction. FIG. 4 is a cross-sectional view taken along the line IV-IV shown in FIG. 3, and is a cross-sectional view of the ultrasound transducer array 50 of the ultrasound observation part 36 of the distal end part 40 taken along a center line of an arc structure.

Figure 3:
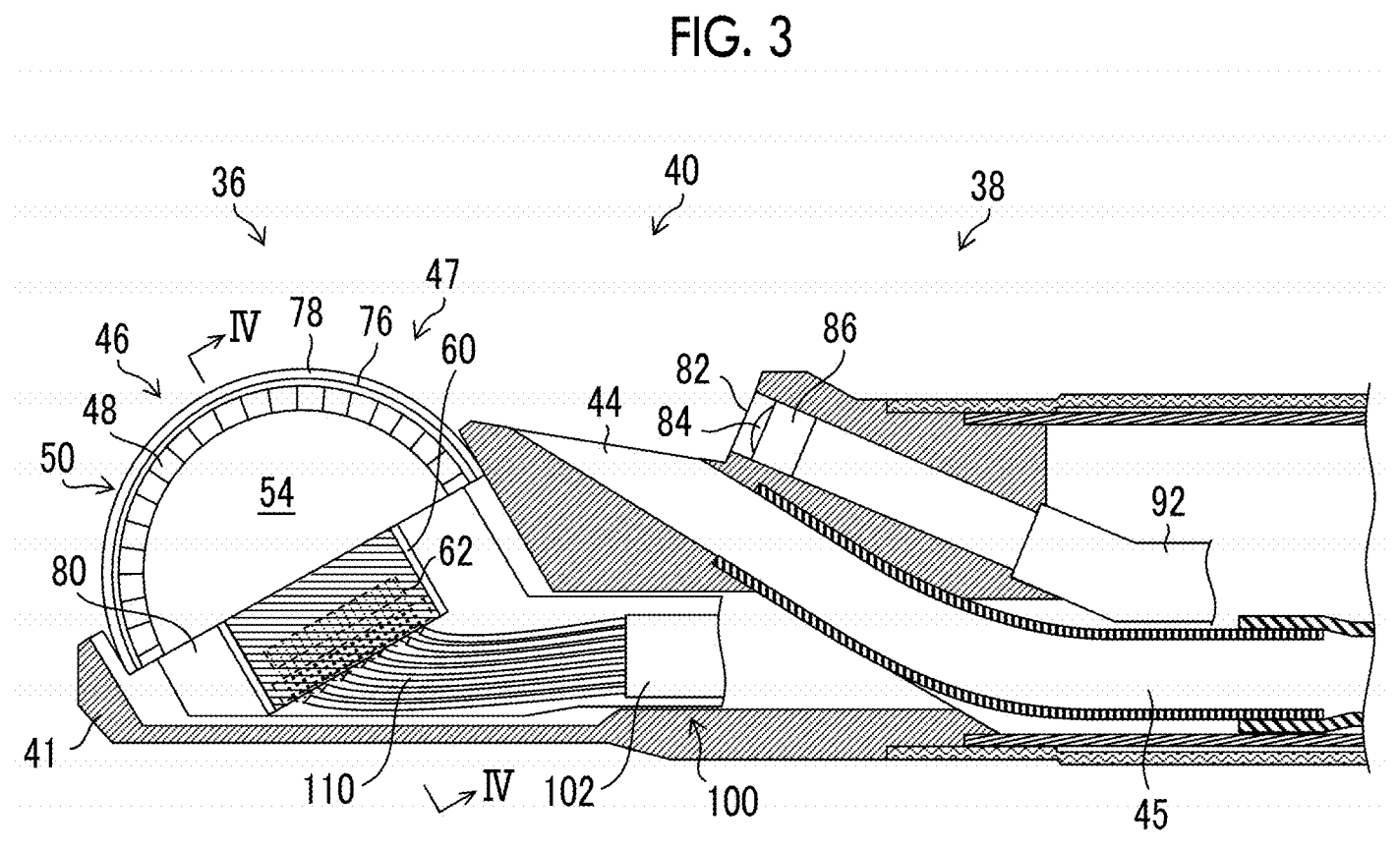

As shown in FIGS. 2 and 3, in the distal end part 40, the ultrasound observation part 36 that acquires an ultrasound image is mounted on the distal end side, and the endoscope observation part 38 that acquires an endoscope image is mounted on the proximal end side. In the distal end part 40, a treatment tool lead-out port 44 is provided between the ultrasound observation part 36 and the endoscope observation part 38.

The endoscope observation part 38 is configured with an observation window 82, an objective lens 84, a solid-state imaging element 86, illumination windows 88, a cleaning nozzle 90, a wiring cable 92, and the like.

The treatment tool lead-out port 44 is connected to a treatment tool channel 45 that is inserted into the insertion part 22. A treatment tool (not shown) inserted from the treatment tool insertion port 30 of FIG. 1 is let out from the treatment tool lead-out port 44 into the body cavity through the treatment tool channel 45.

Figure 4:
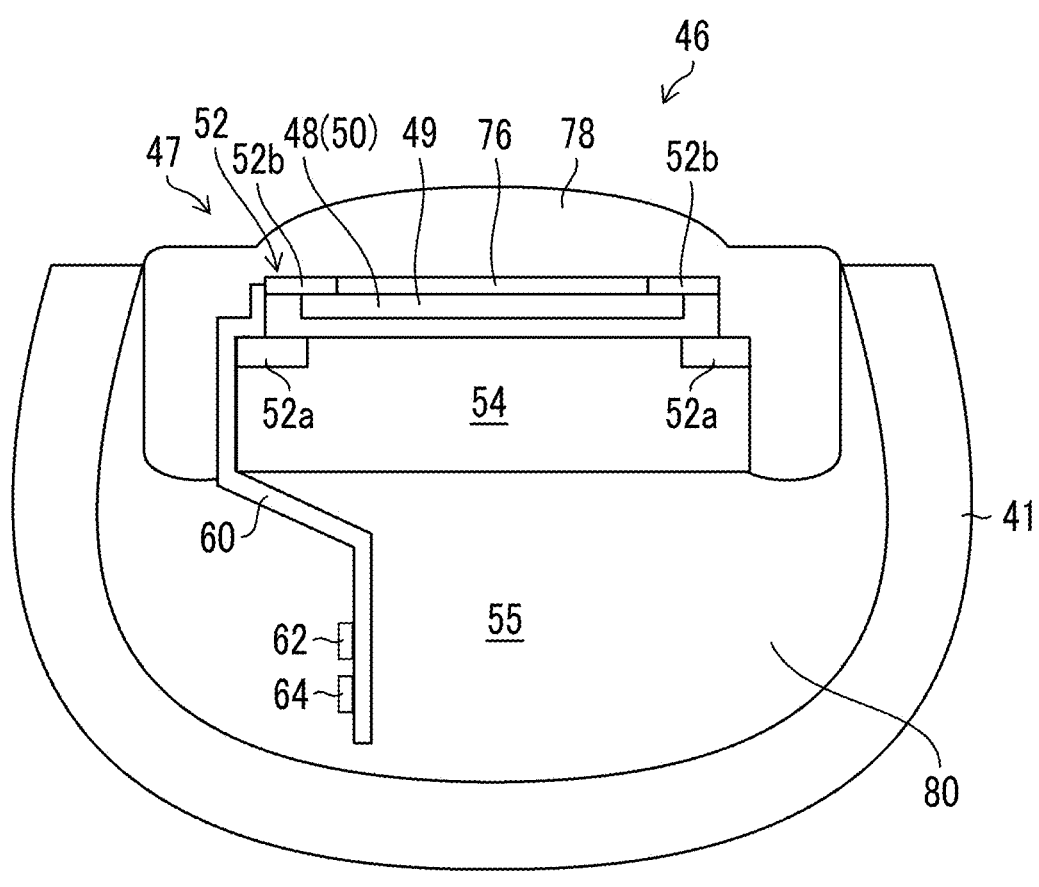
FIG. 4 is a cross-sectional view taken along the line IV-IV shown in FIG. 3.

As shown in FIGS. 2 to 4, the ultrasound observation part 36 comprises the ultrasound transducer unit 46, an exterior member 41 that holds the ultrasound transducer unit 46, and a first cable 100 that is electrically connected to the ultrasound transducer unit 46 through a substrate 60. The exterior member 41 is made of a rigid member, such as rigid resin, and configures a part of the distal end part 40. The first cable 100 is inserted into the insertion part 22 (see FIG. 1).

The ultrasound transducer unit 46 has the ultrasound transducer array 50 that consists of a plurality of ultrasound transducers 48, an electrode 52 that is provided on an end side of the ultrasound transducer array 50 in a width direction (a direction perpendicular to the longitudinal axis direction of the insertion part 22), a backing material layer

54 that supports each ultrasound transducer 48 from a lower surface side, the substrate 60 that is disposed along a side surface of the backing material layer 54 in the width direction and is connected to the electrode 52, and a filler layer 80 with which an internal space 55 between the exterior member 41 and the backing material layer 54 is filled.

As long as the substrate 60 can electrically connect a plurality of ultrasound transducers 48 and the first cable 100, in particular, the structure thereof is not limited.

It is preferable that the substrate 60 is configured with, for example, a wiring substrate, such as a flexible substrate (flexible print substrate (also referred to as a flexible printed circuit (FPC)) having flexibility, a printed wiring circuit substrate (also referred to as a printed circuit board (PCB)) made of a rigid substrate having high rigidity with no flexibility, or a printed wiring substrate (also referred to as a printed wired board (PWB)).

The ultrasound transducer unit 46 has an acoustic matching layer 76 laminated on the ultrasound transducer array 50, and an acoustic lens 78 laminated on the acoustic matching layer 76. That is, the ultrasound transducer unit 46 is configured as a laminate 47 having the acoustic lens 78, the acoustic matching layer 76, the ultrasound transducer array 50, and the backing material layer 54.

The ultrasound transducer array 50 is configured with a plurality of rectangular parallelepiped ultrasound transducers 48 arranged in a convex arc shape outward. The ultrasound transducer array 50 is an array of 48 to 192 channels consisting of 48 to 192 ultrasound transducers 48, for example. Each of the ultrasound transducer 48 has a piezoelectric body 49.

The ultrasound transducer array 50 has the electrode 52. The electrode 52 has an individual electrode 52a individually and independently provided for each ultrasound transducer 48, and a transducer ground 52b that is a common electrode common to all the ultrasound transducers 48. In FIG. 4, a plurality of individual electrodes 52a are disposed on lower surfaces of end portions of a plurality of ultrasound transducers 48, and the transducer ground 52b is disposed on upper surfaces of the end portions of the ultrasound transducers 48.

The substrate 60 has 48 to 192 wirings (not shown) that are electrically connected to the individual electrodes 52a of the 48 to 192 ultrasound transducers 48, respectively, and a plurality of electrode pads 62 that are connected to the ultrasound transducers 48 through the wirings, respectively.

The ultrasound transducer array 50 has a configuration in which a plurality of ultrasound transducers 48 are arranged at a predetermined pitch in a one-dimensional array as an example. The ultrasound transducers 48 configuring the ultrasound transducer array 50 are arranged at regular intervals in a convex bent shape along an axial direction of the distal end part 40 (the longitudinal axis direction of the insertion part 22) and are sequentially driven based on drive signals input from the ultrasound processor device 14 (see FIG. 1). With this, convex electronic scanning is performed with a range where the ultrasound transducers 48 shown in FIG. 2 are arranged, as a scanning range.

The acoustic matching layer 76 is a layer that is provided for taking acoustic impedance matching between the subject and the ultrasound transducers 48.

The acoustic lens 78 is a lens that is provided for converging the ultrasonic waves emitted from the ultrasound transducer array 50 toward the observation target part. The acoustic lens 78 is formed of, for example, silicon-based resin (millable type silicon rubber, liquid silicon rubber, or the lie), butadiene-based resin, or polyurethane-based resin. In the acoustic lens 78, powder, such as titanium oxide, alumina, or silica, is mixed as necessary. With this, the acoustic lens 78 can take acoustic impedance matching between the subject and the ultrasound transducers 48 in the acoustic matching layer 76, and can increase the transmittance of the ultrasonic waves.

As shown in FIGS. 3 and 4, the backing material layer 54 is disposed on an inside with respect to the arrangement surface of a plurality of ultrasound transducers 48, that is, a rear surface (lower surface) of the ultrasound transducer array 50. The backing material layer 54 is made of a layer of a member made of a backing material. The backing material layer 54 has a role of mechanically and flexibly supporting the ultrasound transducer array 50 and attenuating ultrasonic waves propagated to the backing material layer 54 side among ultrasound signals emitted from a plurality of ultrasound transducers 48 or reflected propagated from the observation target. For this reason, the backing material is made of a material having rigidity, such as hard rubber, and an ultrasonic wave attenuation material (ferrite, ceramics, or the like) is added as needed.

The filler layer 80 is a layer with which the internal space 55 between the exterior member 41 and the backing material layer 54 is filled, and has a role of fixing the substrate 60, the first non-coaxial cables 110, and various wiring portions. It is preferable that the acoustic impedance of the filler layer 80 matches the acoustic impedance of the backing material layer 54 with given accuracy or higher such that the ultrasound signals propagated from the ultrasound transducer array 50 to the backing material layer 54 side are not reflected at a boundary surface between the filler layer 80 and the backing material layer 54. It is preferable that the filler layer 80 is made of a member having heat dissipation to increase efficiency in dissipating heat generated in a plurality of ultrasound transducers 48. In a case where the filler layer 80 has heat dissipation, heat is received from the backing material layer 54, the substrate 60, the first non-coaxial cables 110, and the like, and thus, heat dissipation efficiency can be improved.

With the ultrasound transducer unit 46 configured as described above, in a case where each ultrasound transducer 48 of the ultrasound transducer array 50 is driven, and a voltage is applied to the electrode 52 of the ultrasound transducer 48, the piezoelectric body 49 vibrates to sequentially generate ultrasonic waves, and the irradiation of the ultrasonic waves is performed toward the observation target part of the subject. Then, as a plurality of ultrasound transducers 48 are sequentially driven by an electronic switch, such as a multiplexer, scanning with ultrasonic waves is performed in a scanning range along a curved surface on which the ultrasound transducer array 50 is disposed, for example, a range of about several tens mm from the center of curvature of the curved surface.

In a case where the echo signal reflected from the observation target part is received, the piezoelectric body 49 vibrates to generate a voltage and outputs the voltage as an electric signal corresponding to the received ultrasound echo to the ultrasound processor device 14. Then, the electric signal is subjected to various kinds of signal processing in the ultrasound processor device 14 and is displayed as an ultrasound image on the monitor 20.

In the embodiment, the substrate 60 shown in FIG. 4 has, at one end, a plurality of electrode pads 62 that are electrically connected to a plurality of individual electrodes 52a, and a ground electrode pad 64 that is electrically connected to the transducer ground 52b. In FIG. 4, the first cable 100 is omitted.

Electrical bonding of the substrate 60 and the individual electrodes 52a can be established by, for example, a resin material having conductivity. Examples of the resin material include an anisotropic conductive film (ACF) or an anisotropic conductive paste (ACP) obtained by mixing thermosetting resin with fine conductive particles and forming the mixture into a film.

As another resin material, for example, a resin material in which a conductive filler, such as metallic particles, is dispersed into binder resin, such as epoxy or urethane, and the filler forms a conductive path after adhesion may be used. Examples of this resin material include a conductive paste, such as a silver paste.

As shown in FIG. 3, the first cable 100 comprises a plurality of first non-coaxial cables 110, and an outer coat 102 with which a plurality of first non-coaxial cables 110 are coated. Signal wires included in the first non-coaxial cable 110 are electrically bonded to the electrode pads 62 of the substrate 60.

Next, a sectional structure of the first non-coaxial cable 110 will be described referring to FIG. 5, and next, a sectional structure of the first cable 100 will be described referring to FIG. 6. Here, the sectional structure is a structure in sectional view taken along a plane perpendicular to a longitudinal axis direction of the first non-coaxial cable 110 and the first cable 100.

Figure 5:
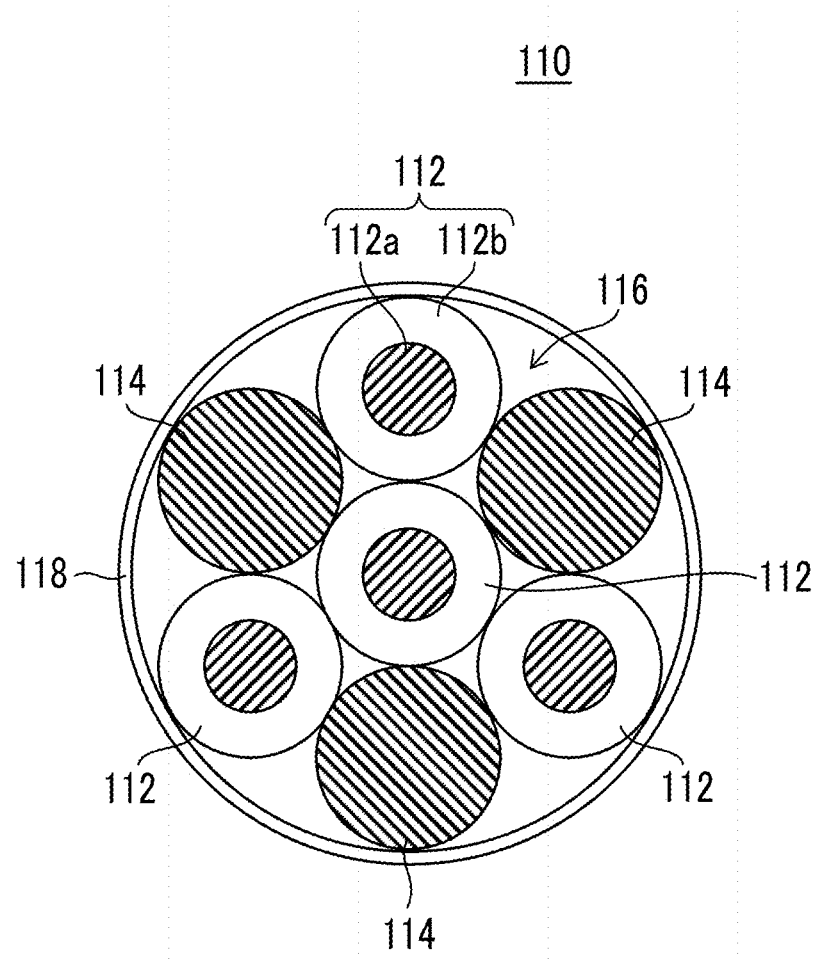
FIG. 5 is a sectional view of a first non-coaxial cable.

As shown in FIG. 5, the first non-coaxial cable 110 has a plurality of signal wires 112 and a plurality of ground wires 114. Each signal wire 112 is made of, for example, a conductor 112a, and an insulating layer 112b with which the periphery of the conductor 112a is coated. The conductor 112a is made of, for example, an element wire, such as copper or copper alloy. The element wire is subjected to, for example, plating processing, such as tin plating or silver plating. The conductor 112a has a diameter of 0.03 mm to 0.04 mm.

The insulating layer 112b can be made of, for example, a resin material, such as fluorinated-ethylene-propylene (FEP) or perfluoroalkoxy (PFA). The insulating layer 112b has a thickness of 0.015 mm to 0.025 mm.

Each ground wire 114 is made of a conductor having the same diameter as the signal wire 112. The ground wire 114 is made of an element wire, such as copper or copper alloy, or a stranded wire obtained by stranding a plurality of element wires, such as copper or copper alloy.

A first cable bundle 116 is configured by stranding a plurality of signal wires 112 and a plurality of ground wires 114.

The first non-coaxial cable 110 comprises a first shield layer 118 with which the periphery of the first cable bundle 116 is coated. The first shield layer 118 can be made of an insulating film obtained by laminating metallic foils through an adhesive. The insulating film is made of a polyethylene terephthalate (PET) film. The metallic foil is made of an aluminum foil or a copper foil.

The first non-coaxial cable 110 is shielded by the first shield layer 118 with a plurality of signal wires 112 as one set. The signal wires 112 are handled in a unit of the first non-coaxial cable 110.

As shown in FIG. 5, in the first non-coaxial cable 110 of the embodiment, the first cable bundle 116 is configured by stranding seven wires in total of four signal wires 112 and three ground wires. One signal wire 112 of the four signal wires 112 is disposed at the center. The remaining three signal wires 112 and the three ground wires 114 are disposed adjacently in the periphery of the signal wire 112 at the center. Note that the number of signal wires 112, the number of ground wires 114, and the disposition of the wires in the first cable bundle 116 are not limited to the structure of FIG. 5.

Figure 6:
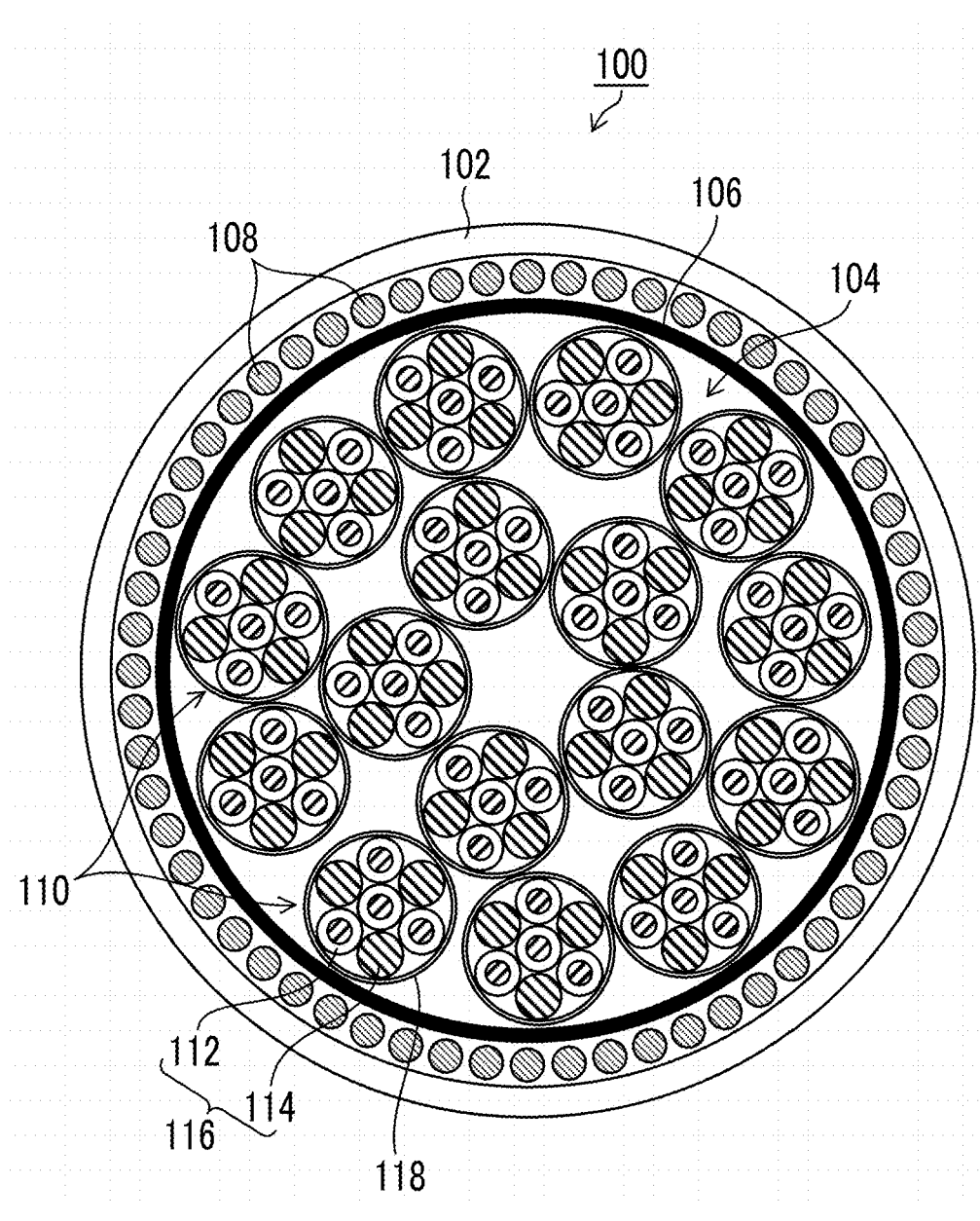
FIG. 6 is a sectional view of a first cable.

Next, as shown in FIG. 6, the first cable 100 comprises a plurality of first non-coaxial cables 110. A second cable bundle 104 is configured with a plurality of first non-coaxial cables 110.

The second cable bundle 104 is coated with the outer coat 102. The outer coat 102 can be made of a fluorine-based resin material, such as extruded and coated PFA, FEP, an ethylene/ethylene tetrafluoride copolymer (ETFE), or polyvinyl chloride (PVC). The outer coat 102 can be made of a wound resin tape (PET tape). The coating of the second cable bundle 104 with the outer coat 102 includes a case where the outside of the second cable bundle 104 is coated directly and a case where the outside of the second cable bundle 104 is coated indirectly. Indirect coating includes disposing another layer between the outer coat 102 and the second cable bundle 104.

The first cable 100 of the embodiment comprises, in order from the inside, a resin layer 106 and a second shield layer 108 between the outer coat 102 and the second cable bundle 104. The second cable bundle 104 is coated with the resin layer 106. The resin layer 106 can be made of, for example, the fluorine-based resin material or the resin tape described above.

The second shield layer 108 may be configured by, for example, braiding a plurality of element wires. The element wire is made of a copper wire, a copper alloy wire, or the like subjected to plating processing (tin plating or silver plating).

The first cable 100 may not comprise both the resin layer 106 and the second shield layer 108 other than the above-described configuration or may comprise only one of the resin layer 106 or the second shield layer 108.

The first cable 100 of the embodiment includes 16 first non-coaxial cables 110, and includes 64 signal wires 112. The number of first non-coaxial cables 110 and the number of signal wires 112 are not limited to the numerical values.

As described above, the first non-coaxial cable 110 included in the first cable 100 does not comprise a shield layer and an outer coat for each signal wire 112, unlike the coaxial cable in the related art. In particular, in a case where the first cable 100 is configured with a plurality of first non-coaxial cables 110, the first cable 100 can be reduced in diameter compared to the coaxial cable in the related art. In a case where the outside diameter is the same as the outside diameter of the coaxial cable, the first cable 100 can comprise a greater number of signal wires 112 than the coaxial cable in the related art.

Figure 7:
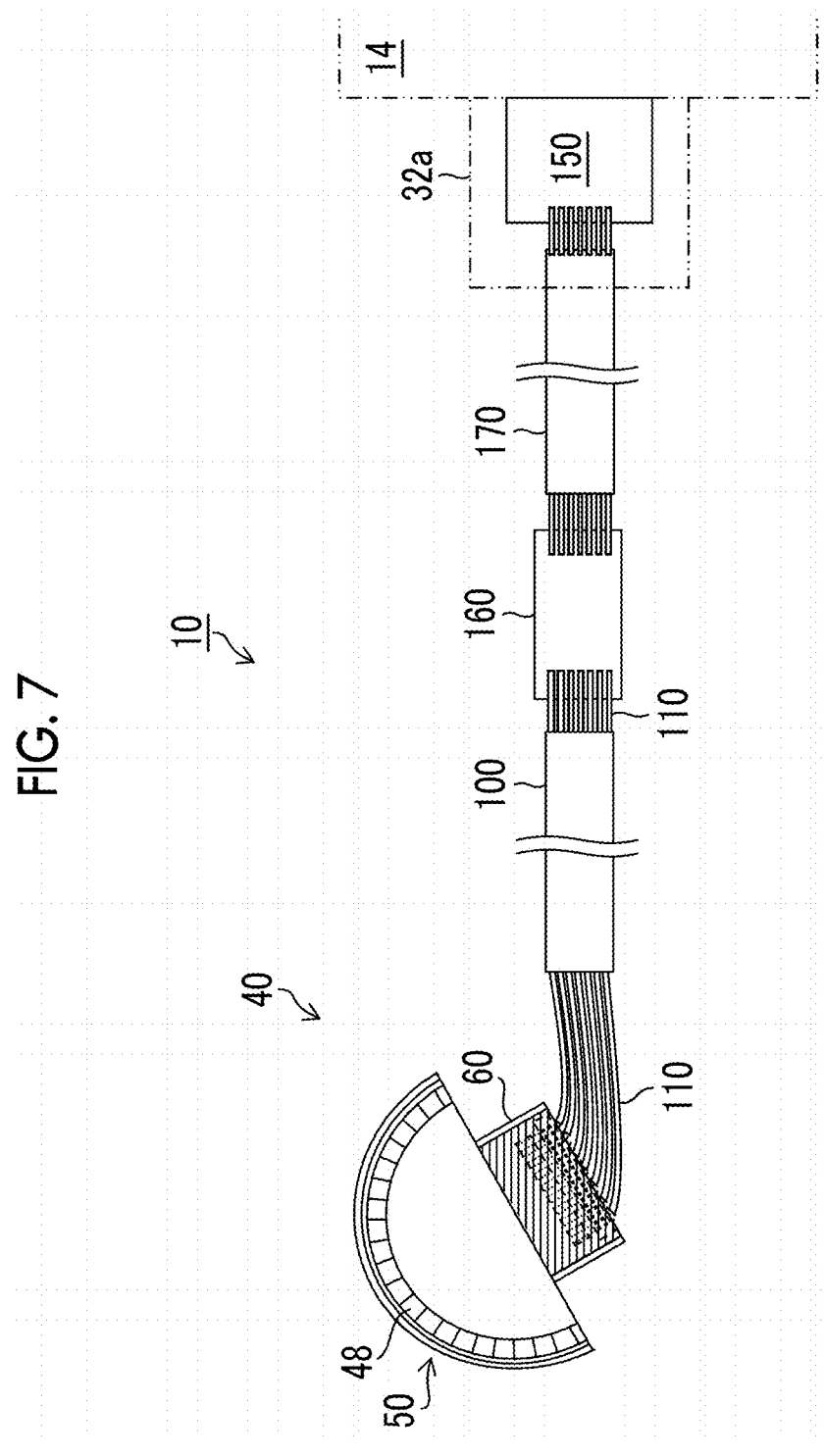
FIG. 7 is a diagram illustrating an electrical connection relationship between ultrasound transducers and an ultrasound processor device in the ultrasonography system.

Next, an electrical connection relationship between the ultrasound transducers 48 and the ultrasound processor device 14 in the ultrasonography system 10 will be described referring to FIG. 7. For transmission and reception of ultrasound signals in the ultrasound transducer array 50, the ultrasound transducers 48 and the ultrasound processor device 14 are electrically connected. For this reason, the ultrasonography system 10 comprises the substrate 60 electrically connected to the ultrasound transducers 48 of the distal end part 40, a connector substrate 150 electrically connected to the ultrasound processor device 14 and disposed in the ultrasound connector 32a, a relay substrate 160 disposed in an electrical path of the substrate 60 and the connector substrate 150, the first cable 100 that electrically connects the substrate 60 and the relay substrate 160, and a second cable 170 that electrically connects the relay substrate 160 and the connector substrate 150, between the ultrasound transducers 48 and the ultrasound processor device 14.

It is preferable that the relay substrate 160 is configured with, for example, a wiring substrate, such as a printed wiring circuit substrate (also referred to as a printed circuit board (PCB)) made of a rigid substrate having high rigidity with no flexibility or a printed wiring substrate (also referred to as a printed wired board (PWB)).

The substrate 60 and the first cable 100 are electrically connected on a distal end side of the first cable 100. A plurality of ultrasound transducers 48 and the first cable 100 are electrically connected by the substrate 60. The signal wires 112 (not shown) of the first non-coaxial cables 110 included in the first cable 100 are electrically bonded to the substrate 60.

The relay substrate 160 and the first cable 100 are electrically connected on a proximal end side of the first cable 100. The signal wires 112 (not shown) of the first non-coaxial cables 110 included in the first cable 100 are electrically bonded to the relay substrate 160.

The relay substrate 160 and the second cable 170 are electrically connected on a distal end side of the second cable 170. The relay substrate 160 electrically connects the proximal end side of the first cable 100 and the distal end side of the second cable 170. On the proximal end side from the first cable 100, the second cable 170 is electrically connected to the connector substrate 150 on a proximal end side of the second cable 170.

An electrical path is formed by the ultrasound transducers 48, the substrate 60, the first cable 100, the relay substrate 160, the second cable 170, the connector substrate 150, and the ultrasound processor device 14.

Next, a connection structure of the substrate 60 and the first cable 100 and a connection structure of the relay substrate 160 and the first cable 100 will be described.

Figure 8:
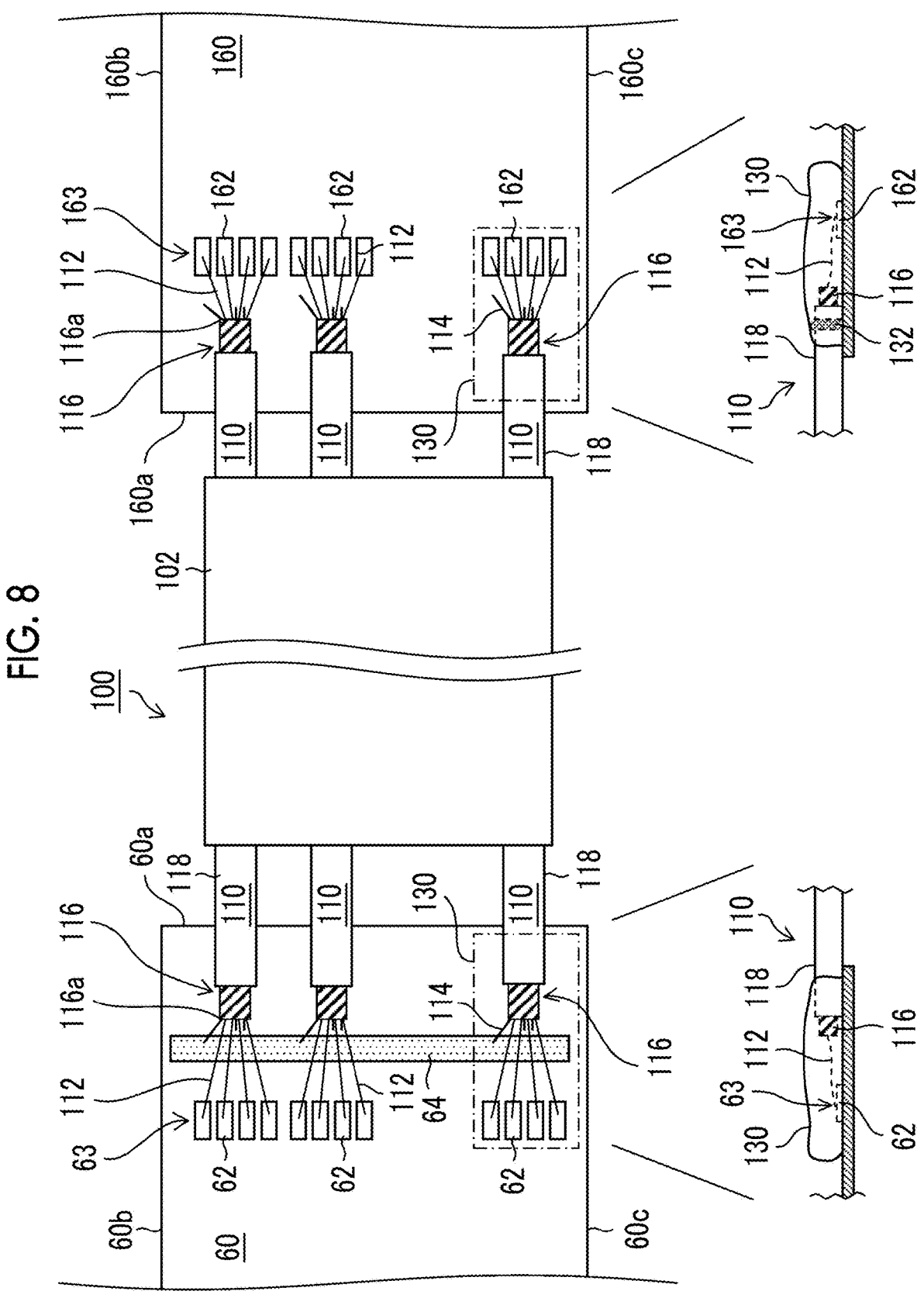
FIG. 8 is a diagram showing a connection structure of a substrate and the first cable and a connection structure of a relay substrate and the first cable.

As shown in FIG. 8, on the side of a side 60a of the substrate 60, the resin layer 106 (not shown), the second shield layer 108 (not shown), and the outer coat 102 of the first cable 100 are removed, and a plurality of first non-coaxial cables 110 are exposed. On the side closer to the side 60a of the substrate 60, the first shield layer 118 of each first non-coaxial cable 110 is removed, and the first cable bundle 116 is exposed. The first non-coaxial cables 110 are disposed in parallel with a side 60b and a side 60c perpendicular to the side 60a.

The substrate 60 and the first shield layer 118 overlap as viewed from a direction perpendicular to the principal surface of the substrate 60 (hereinafter, referred to as plan view). The substrate 60 and the first shield layer 118 may not overlap.

The first cable bundle 116 configured with a stranded wire of a plurality of signal wires 112 and a plurality of ground wires 114 is unstranded into the respective signal wires 112 at a distal end 116a. The unstranded signal wires 112 are electrically bonded to the electrode pads 62 disposed on the substrate 60, and a plurality of first electrical bonded portions 63 are formed. The distal end 116a is a start position where each signal wire 112 is unstranded.

As shown in FIG. 8, the electrode pads 62 corresponding to each first non-coaxial cable 110 are collectively disposed. That is, the first electrical bonded portions 63 of four signal wires 112 and four electrode pads 62 are collectively disposed on the substrate 60 for each first cable bundle 116. To avoid disconnection of the signal wires 112 of the first non-coaxial cable 110, a distance between the first non-coaxial cable 110 and the electrode pads 62 is made short.

It is preferable that a fixing member 130 that protects the first electrical bonded portions 63 is provided in the first electrical bonded portions 63 to prevent disconnection of the signal wires 112 even in a case where a large load is applied to the first electrical bonded portions 63. It is preferable that the fixing member 130 is a member having high rigidity (rigid). It is preferable that the fixing member 130 is an insulating resin layer by adhesive curing or the like, a metal, or a resin member having high hardness. In particular, in a case where the fixing member 130 is a metal, radiation electromagnetic waves can be suppressed. In some first cable bundles 116, the fixing member 130 on the substrate 60 is omitted for ease of understanding.

The ground electrode pad 64 is disposed on the substrate 60 separately from the electrode pads 62. The ground wires 114 included in the first cable bundle 116 are electrically bonded to the ground electrode pad 64. The ground wires 114 are electrically bonded to the ground electrode pad 64, whereby the ground potentials of a plurality of first cable bundles 116 can be at the same potential. At least one ground wire 114 of a plurality of ground wires 114 may be electrically bonded to the ground electrode pad 64. This is because a plurality of ground wires 114 are in contact with each other in the first cable bundle 116. A region occupied by the wires can be reduced by reducing the number of ground wires 114 that are electrically bonded to the ground electrode pad 64.

On the side of a side 160a of the relay substrate 160, the first shield layer 118 of each first non-coaxial cable 110 is removed, and the first cable bundle 116 is exposed. The first non-coaxial cable 110 is disposed in parallel with a side 160b and a side 160c perpendicular to the side 160a. The relay substrate 160 comprises first cable-side electrode pads 162 corresponding to the signal wires 112 included in the first cable bundle 116. The signal wires 112 of the first non-coaxial cables 110 and the first cable-side electrode pads 162 are electrically bonded, and second electrical bonded portions 163 are formed.

As shown in FIG. 8, the first cable-side electrode pads 162 corresponding to each first non-coaxial cable 110 are collectively disposed. That is, the second electrical bonded portions 163 formed by the four signal wires 112 and four first cable-side electrode pads 162 are collectively disposed on the relay substrate 160 for each first cable bundle 116. To avoid disconnection of the signal wires 112 of the first non-coaxial cable 110, a distance between the first non-coaxial cable 110 and the first cable-side electrode pads 162 is made short.

Similarly to the first electrical bonded portions 63, it is preferable that a fixing member 130 that reinforces the second electrical bonded portions 163 is provided in the second electrical bonded portions 163 to prevent disconnection of the signal wires 112 even in a case where a large load is applied to the second electrical bonded portions 163. It is preferable that the fixing member 130 is a member having high rigidity (rigid). It is preferable that the fixing member 130 is an insulating resin layer by adhesive curing or the like, a metal, or a resin member having high hardness. In particular, in a case where the fixing member 130 is a metal, radiation electromagnetic waves can be suppressed. In some first cable bundles 116, the fixing member 130 on the relay substrate 160 is omitted for ease of understanding.

In a case where the fixing member 130 is a metallic member, for example, it is preferable that the fixing member 130 is electrically connected to the first shield layer 118 through a connecting member 132.

Figure 9:
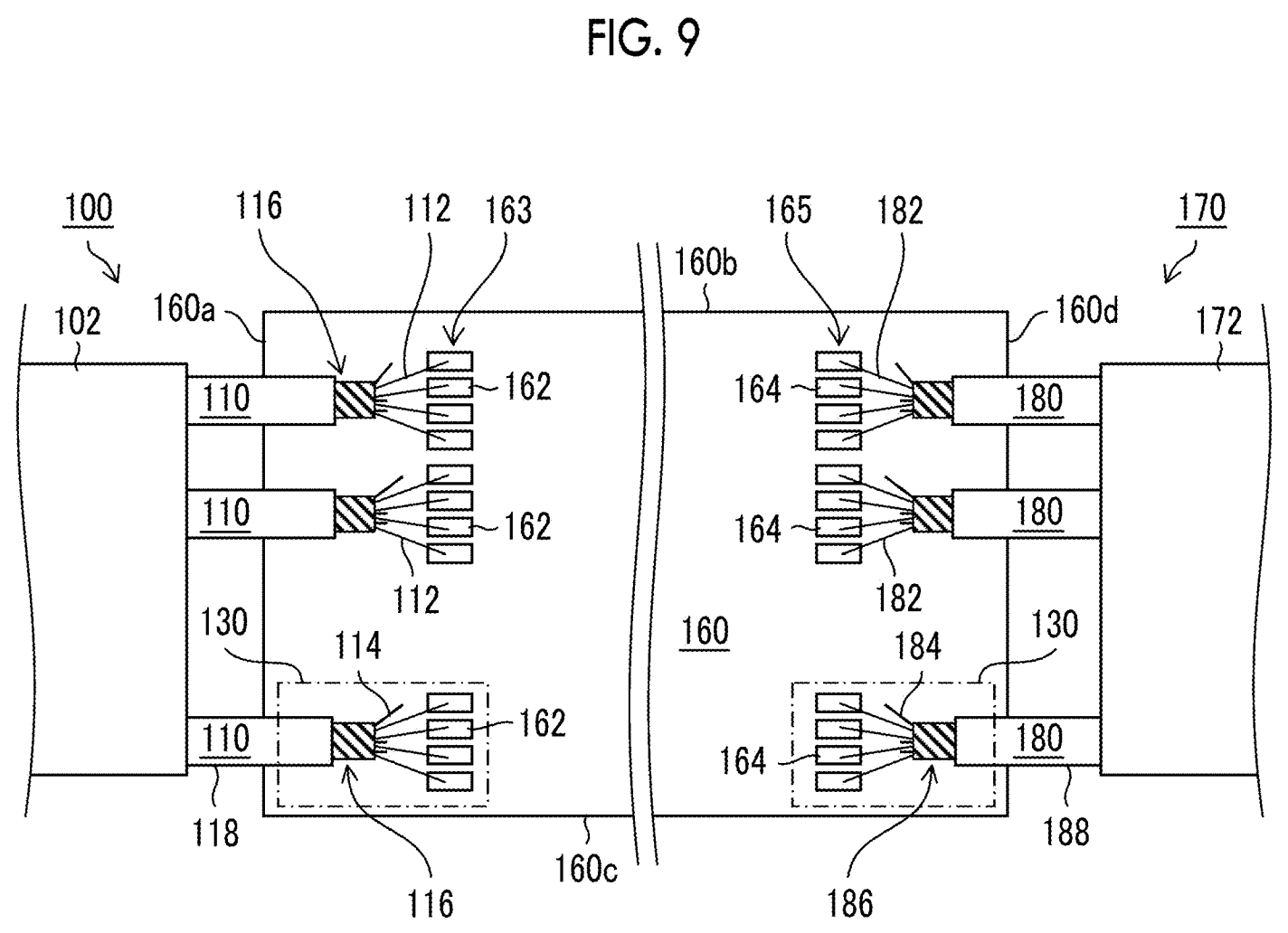

Next, a connection structure of the relay substrate 160 and the second cable 170 will be described. As shown in FIG. 9, the relay substrate 160 comprises second cable-side electrode pads 164 for electrical connection to the second cable 170 on a proximal end side. The second cable-side electrode pads 164 are disposed along a side 160d.

The second cable 170 has the same structure as the first cable 100. The second cable 170 includes a plurality of second non-coaxial cables 180. A fourth cable bundle (not shown) is configured with a plurality of second non-coaxial cables 180. The fourth cable bundle corresponds to the second cable bundle 104 of the first cable 100.

The second cable 170 comprises an outer coat 172 that covers a plurality of second non-coaxial cables 180. The outer coat 172 is configured with the same material and structure as the outer coat 102 of the first cable 100.

Each second non-coaxial cable 180 has the same configuration as the first non-coaxial cable 110, and has a plurality of signal wires 182 and a plurality of ground wires 184. Each signal wire 182 is made of, for example, a conductor (not shown) and an insulating layer (not shown) with which the periphery of the conductor is coated. The conductor and the insulating layer of the second non-coaxial cable 180 are configured with the same material and structure as the conductor 112a and the insulating layer 112b of the first non-coaxial cable 110, respectively. A third cable bundle 186 is configured by stranding a plurality of signal wires 182 and a plurality of ground wires 184. The third cable bundle 186 corresponds to the first cable bundle 116 of the first non-coaxial cable 110.

Each second non-coaxial cable 180 comprises a second shield layer 188 with which the periphery of the third cable bundle 186 is coated. The second shield layer 188 is configured with the same material and structure as the first shield layer 118 of the first non-coaxial cable 110.

The second cable 170 can comprise a resin layer and a second shield layer configured with the same material and structure as the resin layer 106 and the second shield layer 108 of the first cable 100, respectively.

On the side of the side 160d of the relay substrate 160, the second shield layer 188 of each second non-coaxial cable 180 is removed, and the third cable bundle 186 is exposed. The second non-coaxial cables 180 are disposed in parallel with the side 160b and the side 160c. The relay substrate 160 comprises the second cable-side electrode pads 164 corresponding to the signal wires 182 included in the third cable bundles 186. The signal wires 182 of the second non-coaxial cables 180 and the second cable-side electrode pads 164 are electrically bonded, and third electrical bonded portions 165 are formed.

As shown in FIG. 9, the second cable-side electrode pads 164 corresponding to each second non-coaxial cable 180 are collectively disposed. That is, the third electrical bonded portions 165 formed by the four signal wires 182 and four second cable-side electrode pads 164 are collectively disposed on the relay substrate 160 for each third cable bundle 186.

Similarly to the second electrical bonded portions 163, it is preferable that a fixing member 130 that reinforces the third electrical bonded portions 165 is provided in the third electrical bonded portions 165.

Figure 10:
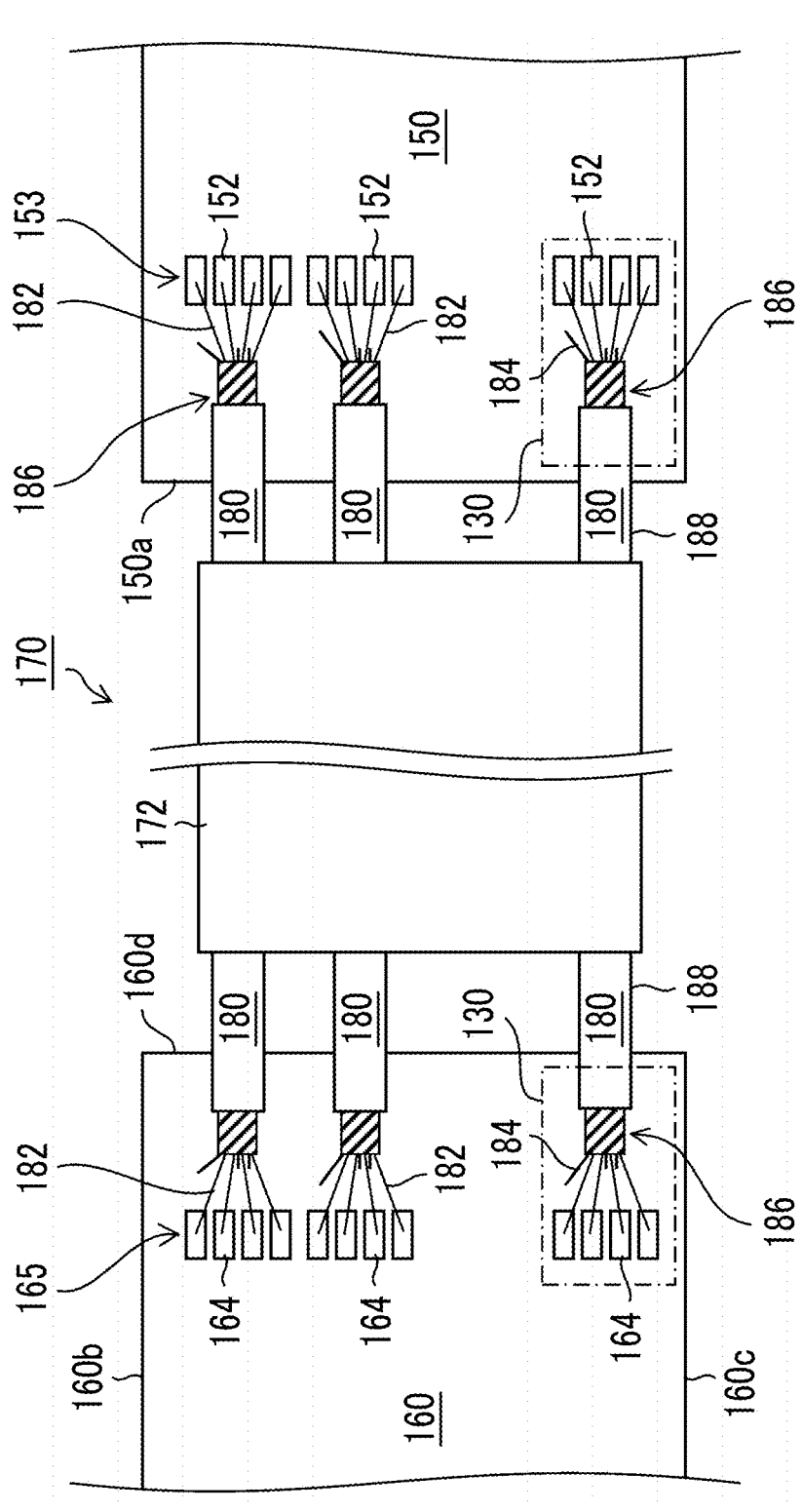
FIG. 10 is a diagram showing a connection structure of a connector substrate and the second cable.

Next, a connection structure of the connector substrate 150 and the second cable 170 will be described. As shown in FIG. 10, on the side of a side 150a of the connector substrate 150, the second shield layer 188 of each second non-coaxial cable 180 is removed, and the third cable bundle 186 is exposed.

The connector substrate 150 comprises connector electrode pads 152 corresponding to the signal wires 182 included in the third cable bundle 186. The connector electrode pads 152 are disposed along the side 150a. The signal wires 182 of the second non-coaxial cable 180 and the connector electrode pads 152 are electrically bonded, and fourth electrical bonded portions 153 are formed.

As shown in FIG. 10, the connector electrode pads 152 corresponding to each second non-coaxial cable 180 are collectively disposed. That is, the fourth electrical bonded portions 153 formed by the four signal wires 182 and four connector electrode pads 152 are collectively disposed on the connector substrate 150 for each third cable bundle 186.

It is preferable that a fixing member 130 that protects the fourth electrical bonded portions 153 is provided in the fourth electrical bonded portions 153.

Figure 11:
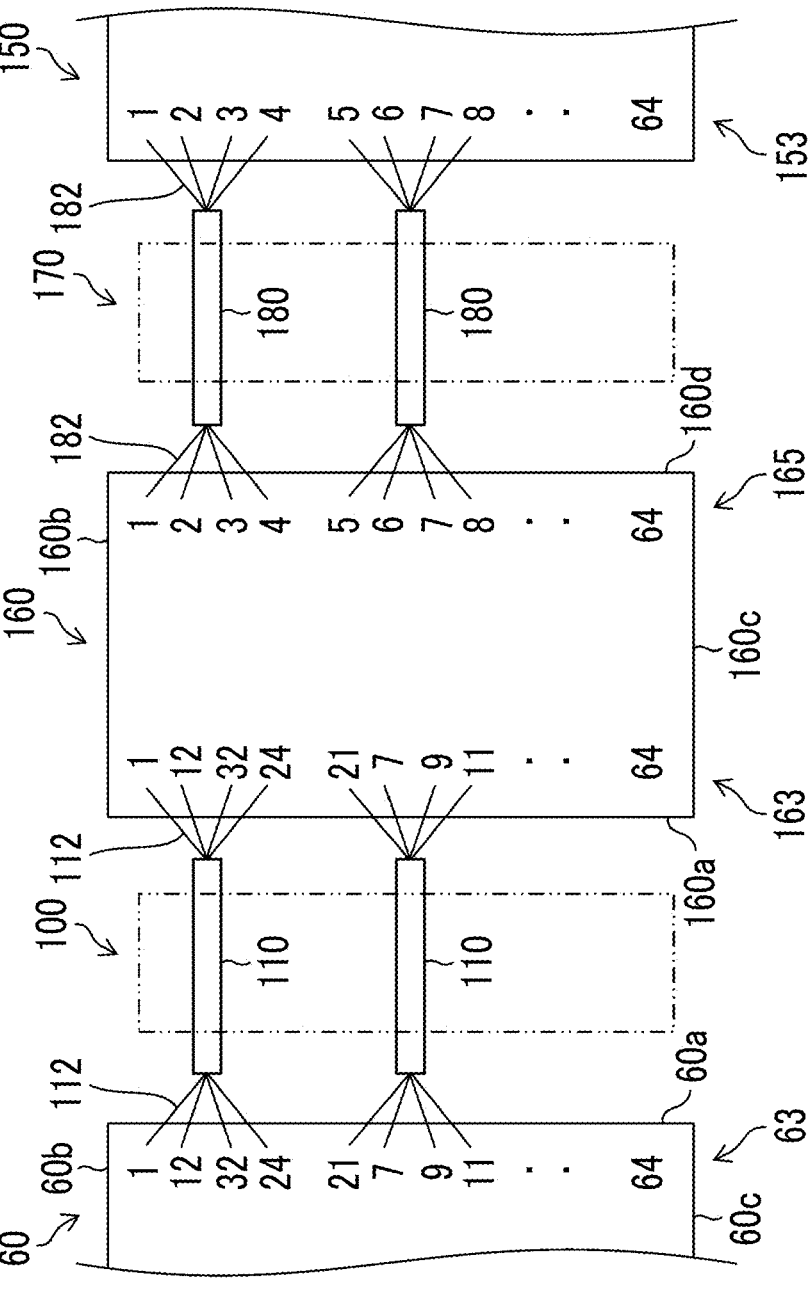
FIG. 11 is a diagram showing a first form of an electrical path between the substrate and the connector substrate.

Next, a first form of an electrical path between the substrate 60 and the connector substrate 150 will be described referring to FIG. 11. Between the ultrasound transducers 48 and the ultrasound processor device 14, an electrical path is formed through the substrate 60, the first cable 100, the relay substrate 160, the second cable 170, and the connector substrate 150.

For the ultrasound processor device 14 to make the drive target ultrasound transducers 48 transmit and receive ultrasound signals, the ultrasound processor device 14 and each ultrasound transducer 48 are electrically connected in a one-to-one correspondence relationship.

For example, to identify each ultrasound transducer, element numbers (1 to N) are given to the ultrasound transducers 48. The electrode of the ultrasound transducer 48 corresponding to the element number and the electrode of the ultrasound processor device 14 having an electrode number corresponding to the element number are electrically connected in a one-to-one correspondence relationship.

Incidentally, in an actual ultrasound endoscope 12, the electrode pads 62 of the substrate 60 electrically connected to the ultrasound transducers 48 are configured in a decided disposition to suppress the occurrence of crosstalk, for example. On the other hand, the disposition of the connector electrode pads 152 of the connector substrate 150 is configured in a disposition decided by the ultrasound processor device 14 that is connected to the connector substrate 150. In particular, in a case where the first cable 100 including the first non-coaxial cables 110 and the second cable 170 including the second non-coaxial cables 180 are applied, it is important to match the disposition between the electrode pads (the electrode pads 62 and the connector electrode pads 152) of the substrate 60 and the connector substrate 150.

Here, 64 ultrasound transducers 48 will be described as an example. As shown in FIG. 11, the electrode pads 62 (not shown) on the side of the ultrasound transducers 48 on the substrate 60 are configured in a decided disposition. For example, the first electrical bonded portions 63 are disposed in an order of "1", "12", "32", "24", "21", "7", "9", "11", . . . , and "64" corresponding to the element numbers of the ultrasound transducers 48 on the substrate 60. Each first electrical bonded portion 63 is electrically connected to the ultrasound transducer 48 corresponding to the element number in the distal end part 40 (not shown).

On the other hand, the fourth electrical bonded portions 153 are disposed in an order of "1", "2", "3", "4", "5", "6", "7", "8", . . . , and "64" corresponding to the electrode numbers of the electrodes of the ultrasound processor device 14 on the connector substrate 150. In the first electrical bonded portions 63 and the fourth electrical bonded portions

153, common numbers (the element numbers and the electrode numbers) are electrically connected.

A case where the substrate 60 and the connector substrate 150 are electrically connected with only the first cable 100 including the first non-coaxial cables 110 is also considered. However, in the first non-coaxial cable 110, the four signal wires 112 need to be handled as one set, and in a case where the disposition of the electrode pads is different between the substrate 60 and the connector substrate 150, there is a concern that connection is difficult.

Accordingly, in the embodiment, the relay substrate 160 is applied. As shown in FIG. 11, the substrate 60 and the relay substrate 160 are electrically connected by the first cable 100. A plurality of first electrical bonded portions 63 and a plurality of second electrical bonded portions 163 corresponding to each first non-coaxial cable 110 are electrically connected in a one-to-one correspondence relationship, and are each collectively disposed. As a result, in comparison of a plurality of first electrical bonded portions 63 with a plurality of second electrical bonded portions 163, the disposition order is identical or is substantially identical.

In a unit of the first non-coaxial cable 110, in a case where a disposition order of a plurality of first electrical bonded portions 63 coincides with a disposition order of a plurality of second electrical bonded portions 163, it can be said that the disposition orders are identical. In the embodiment, this case refers to a case where the first electrical bonded portions 63 are in an order of "1", "12", "32", and "24", and the second electrical bonded portions 163 are in an order of "1", "12", "32", and "24".

In a unit of the first non-coaxial cable 110, even in a case where a plurality of first electrical bonded portions 63 and a plurality of second electrical bonded portions 163 each collectively disposed are different in the disposition order, it can be said that the disposition orders are substantially identical. For example, this refers to a case where the first electrical bonded portions 63 are in an order of "1", "12", "32", and "24", and the second electrical bonded portions 163 are in an order of "1", "32", "24", and "12". This is because, in the first non-coaxial cable 110, as long as the four signal wires 112 are handled as one set, the disposition order is allowed to be different between the first electrical bonded portions 63 and the second electrical bonded portions 163.

In a unit of the first non-coaxial cable 110, even in a case where a plurality of first electrical bonded portions 63 and a plurality of second electrical bonded portions 163 each collectively disposed are different in positions on the substrate 60 and the relay substrate 160, it can be said that the disposition orders are substantially identical.

For example, this case refers to a case where the first electrical bonded portions 63 are disposed in an order of "1", "12", "32", and "24" at positions close to the side 60b of the substrate 60, and the second electrical bonded portions 163 are disposed in an order of "1", "12", "32", and "24" at positions close to the side 160c of the relay substrate 160. This is because, in the first non-coaxial cable 110, as long as the four signal wires 112 are handled as one set, the positions of the first electrical bonded portions 63 on the substrate 60 are allowed to be different from the positions of the second electrical bonded portions 163 on the relay substrate 160.

The connector substrate 150 and the relay substrate 160 are electrically connected by the second cable 170. A plurality of third electrical bonded portions 165 and a plurality of fourth electrical bonded portions 153 corresponding to each second non-coaxial cable 180 are electrically connected in a one-to-one correspondence relationship, and are each collectively disposed. As a result, in comparison of a plurality of third electrical bonded portions 165 and a plurality of fourth electrical bonded portions 153, the disposition orders are identical or are substantially identical.

A plurality of third electrical bonded portions 165 and a plurality of fourth electrical bonded portions 153 can be in the same disposition orders as a plurality of first electrical bonded portions 63 and a plurality of second electrical bonded portions 163 described above.

The first cable 100 and the second cable 170 are electrically connected to the relay substrate 160. A plurality of second electrical bonded portions 163 and a plurality of third electrical bonded portions 165 are disposed in different arrangement orders. This is because a plurality of second electrical bonded portions 163 reflects the disposition of the electrode pads 62 on the ultrasound transducers 48 side, and a plurality of third electrical bonded portions 165 reflects the disposition of the connector electrode pads 152 on the ultrasound processor device 14 side. On the other hand, the relay substrate 160 can electrically connect a plurality of second electrical bonded portions 163 and a plurality of third electrical bonded portions 165 in different arrangement orders in a one-to-one correspondence relationship. The relay substrate 160 electrically connects the second electrical bonded portions 163 and the third electrical bonded portions 165 by wirings (not shown) such that corresponding element numbers and electrode numbers coincide with each other. With the application of the relay substrate 160, even in a case where the disposition of the electrode pads is different between the substrate 60 and the connector substrate 150, the ultrasound transducers 48 and the ultrasound processor device 14 can be electrically connected using the non-coaxial cables (the first non-coaxial cables 110 and the second non-coaxial cables 180).

Next, a second form of an electrical path between the substrate 60 and the connector substrate 150 will be described referring to FIG. 12. In the second form of the electrical path, a second cable 190 having a different structure from the second cable 170 is applied. The second cable 190 is configured by putting together a plurality of coaxial cables 192 each having a signal wire 194, for example, with an outer coat 196. Each coaxial cable 192 comprises, for example, the signal wire 194 at the center side, and is configured with an insulating outer coat provided in a layer outside the signal wire 194, a shield layer provided in a layer outside the outer coat, and an insulating outer coat provided in the outermost layer.

Figure 12:
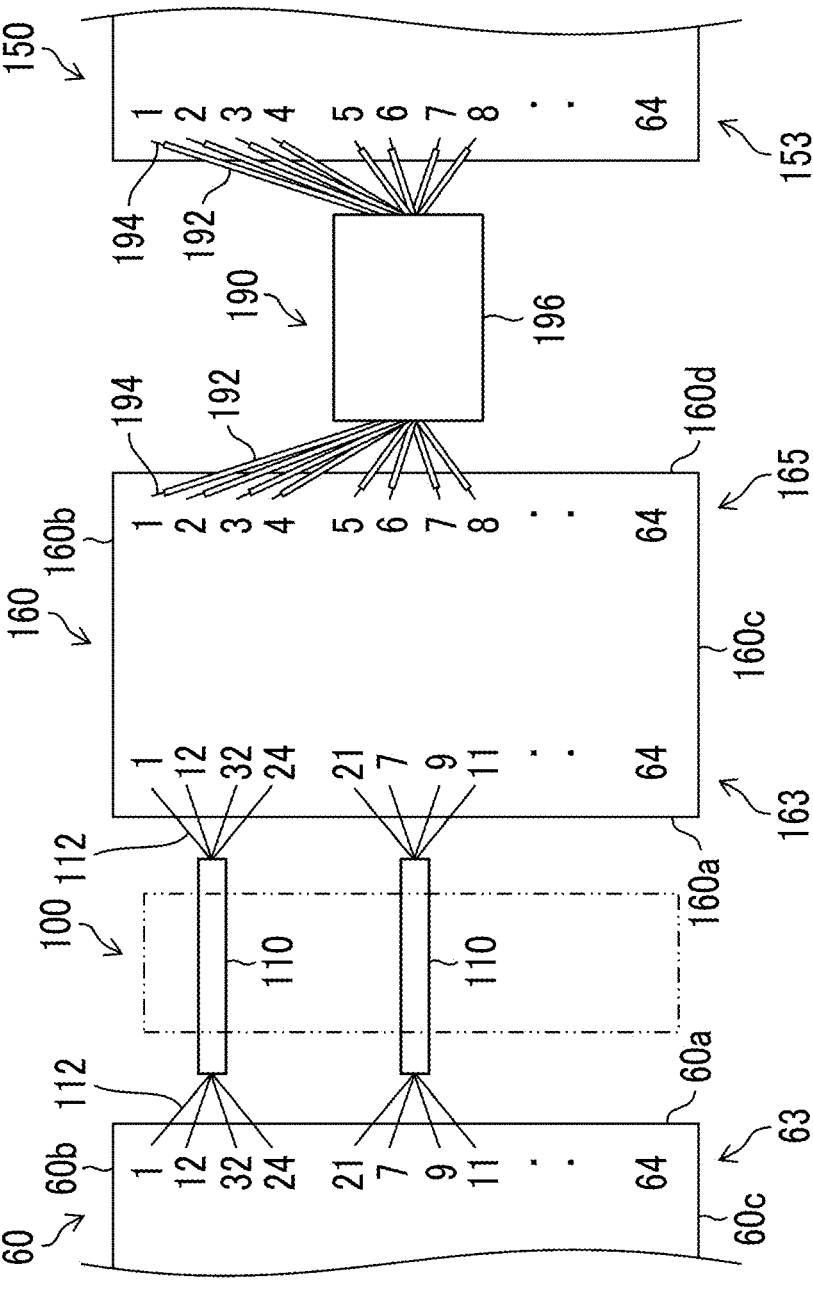
FIG. 12 is a diagram showing a second form of an electrical path between the substrate and the connector substrate.

As shown in FIG. 12, the relay substrate 160 and the connector substrate 150 are electrically connected by the second cable 190. Similarly to the first form of the electrical path, the relay substrate 160 can electrically connect a plurality of second electrical bonded portions 163 and a plurality of third electrical bonded portions 165 in different arrangement orders, in a one-to-one correspondence relationship.

In a case where the second cable 190 is configured with a plurality of coaxial cables 192, in regard to the arrangement of the disposition, the third electrical bonded portions 165 and the fourth electrical bonded portions 153 can be disposed without limit. This is because the coaxial cable 192 has a structure hard to be disconnected, and accordingly, the third electrical bonded portions 165 and the fourth electrical bonded portions 153 can be freely electrically connected even in a case the arrangement of the disposition is different.

In the first form and the second form of the electrical path, since one relay substrate 160 is applied, the structure is simple, the number of components can be reduced, and the relay substrate 160 is reduced in size.

It is preferable that the signal wires 182 included in the second cable 170 and the signal wires 194 included in the second cable 190 have a greater outside diameter, a longer outer peripheral length, or both a greater outside diameter and a longer outer peripheral length than the signal wires 112 included in the first cable 100. The signal wires 182 and the signal wires 194, and the signal wires 112 have the above-described relationship, whereby it is possible to reduce attenuation of ultrasound signals in the whole electrical path. This is because, in general, signal wires having a large outside diameter, a long outer peripheral length, or both a large outside diameter and a long outer peripheral length can make an attenuation factor small. In particular, since the magnitude of the outside diameter or the like of the signal wires is not limited in parts not entering a human body, the above-described configuration can be applied to the signal wires 182 or 194 of the second cable 170 or 190.

Figure 13A:
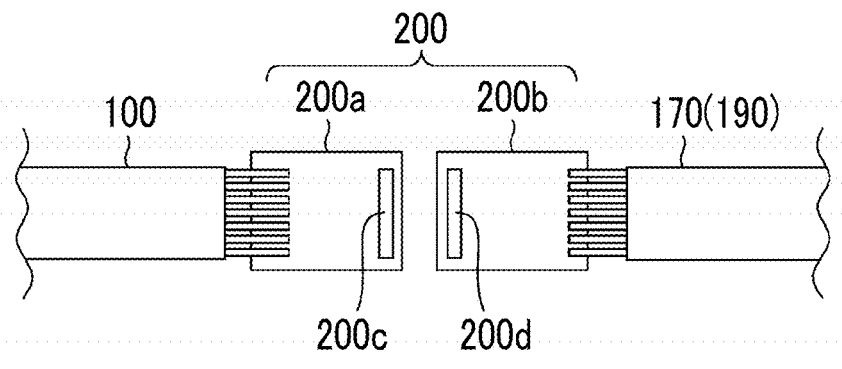
FIGS. 13A and 13B are diagrams showing another form of a relay substrate.
Figure 13B:
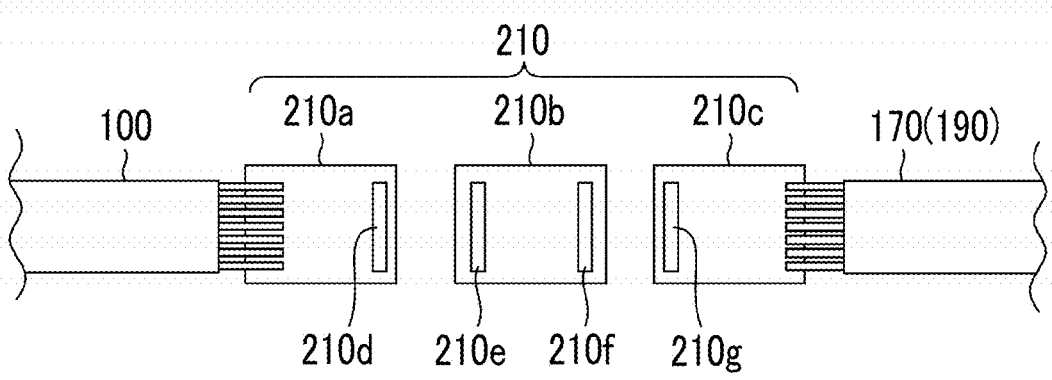

Next, a preferred form of a relay substrate will be described referring to FIGS. 13A and 13B. FIG. 13A is a diagram showing a first form of a relay substrate, and FIG. 13B is a diagram showing a second form of a relay substrate. The relay substrates of FIGS. 13A and 13B can be configured with a plurality of attachable and detachable relay substrates.

As shown in FIG. 13A, a relay substrate 200 is configured with a first relay substrate 200a and a second relay substrate 200b. The first relay substrate 200a comprises a substrate connector 200c. The second relay substrate 200b comprises a substrate connector 200d. In the relay substrate 200, the first relay substrate 200a and the second relay substrate 200b are configured to be attachable and detachable through the substrate connector 200c and the substrate connector 200d. The substrate connector 200c and the substrate connector 200d can be electrically connected with a cable (not shown).

As shown in FIG. 13B, a relay substrate 210 is configured with a first relay substrate 210a, a second relay substrate 210b, and a third relay substrate 210c. The first relay substrate 210a comprises a substrate connector 210d. The second relay substrate 210b comprises a substrate connector 210e and a substrate connector 210f. The third relay substrate 210c comprises a substrate connector 210g. The first relay substrate 210a and the second relay substrate 210b are configured to be attachable and detachable through the substrate connector 210d and the substrate connector 210e. The second relay substrate 210b and the third relay substrate 210c are configured to be attachable and detachable through the substrate connector 210f and the substrate connector 210g. The substrate connector 210d and the substrate connector 210e, and the substrate connector 210f and the substrate connector 210g can be electrically connected with cables (not shown).

With the relay substrates 200 and 210 of FIGS. 13A and 13B, since the ultrasound transducers 48 side and the ultrasound processor device 14 side can be separated, it is possible to replace only necessary components, for example, at the time of maintenance or repair. It is also possible to reduce the size of only the first relay substrate 200a or 210a that is electrically connected to the first cable 100. It is possible to achieve reduction in diameter of the ultrasound endoscope 12.

Figure 14A:
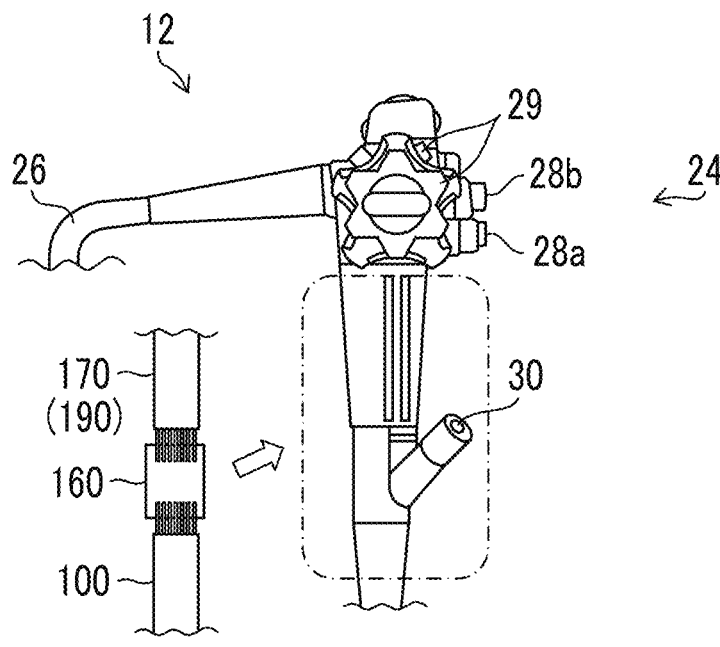
FIGS. 14A and 14B are diagrams showing a preferred disposition position of the relay substrate.

Next, a preferred disposition position of a relay substrate will be described referring to FIGS. 14A and 14B. FIG. 14A is a diagram showing a first form of a disposition position of

Figure 14B:
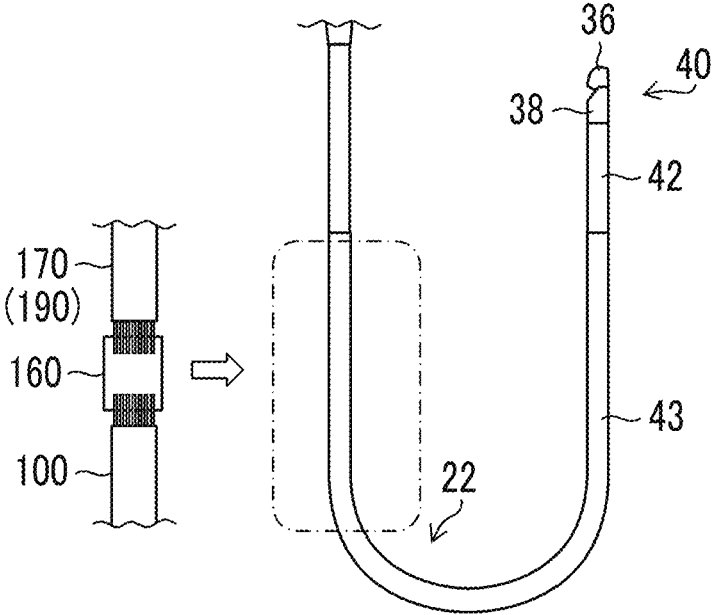

17 the relay substrate 160, and FIG. 14B is a diagram showing a second form of a disposition position of the relay substrate 160.

As shown in FIG. 14A, the relay substrate 160 is disposed inside the operating part 24 of the ultrasound endoscope 12 surrounded by a one-dot chain line. Since the operating part 24 has a comparatively wide space, the disposition of the relay substrate 160 is facilitated. In a case where the relay substrate is disposed in the operating part 24, not only the relay substrate 160 made of one substrate, but also the attachable and detachable relay substrates 200 and 210 shown in FIGS. 13A and 13B can be applied.

As shown in FIG. 14B, the relay substrate 160 is disposed on the proximal end side from the distal end part 40 in the insertion part 22. For example, the relay substrate 160 can be disposed inside the flexible part 43 surrounded by a one-dot chain line.

Next, insulation coating members 134 with which the relay substrate 160 is coated will be described referring to FIGS. 15A to 15C.

Figure 15A:
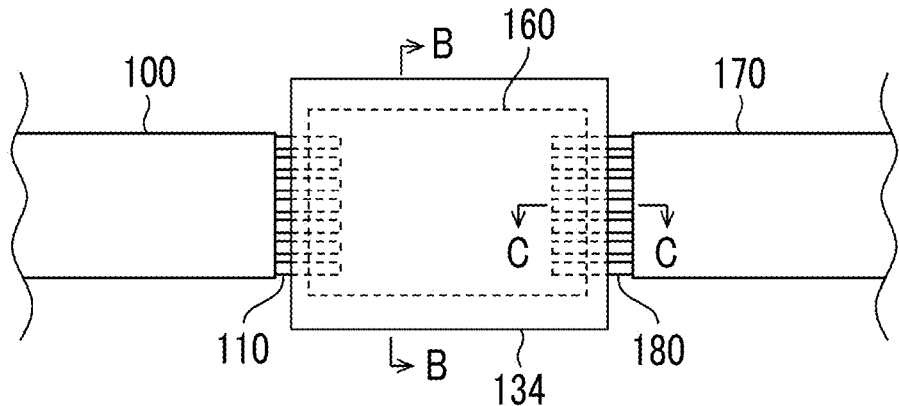
Figure 15A:
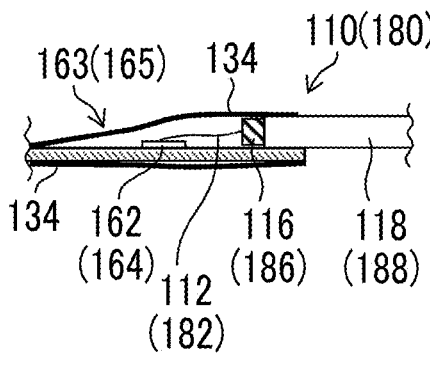

FIG. 15A is a plan view of the relay substrate 160, FIG. 15B is a sectional view taken along the line B-B, and FIG. 15C is a sectional view taken along the line C-C.

Since the ultrasound transducers 48 (not shown) are driven with a high voltage of about 40 V, as shown in FIG. 15A, it is preferable that the relay substrate 160 is coated with the insulation coating members 134.

As shown in FIG. 15B, the insulation coating members 134 are, for example, an insulating tape. The relay substrate 160 can be sandwiched by the insulation coating members 134 from both sides. An insulating tube other than the insulating tape can be applied as the insulation coating members 134.

As shown in FIG. 15C, it is preferable that the second electrical bonded portions 163 and the third electrical bonded portions 165 are coated with the insulation coating members 134. Similarly to FIG. 15B, safety is improved. It is preferable that the insulation coating members 134 have a dielectric breakdown voltage equal to or greater than 2 kV.

Although the invention has been described, the invention is not limited to the above-described example, and various improvements or modifications may be of course made without departing from the spirit and scope of the invention.

EXPLANATION OF REFERENCES

10: ultrasonography system
12: ultrasound endoscope
14: ultrasound processor device
16: endoscope processor device
18: light source device
20: monitor
21*a*: water supply tank
21*b*: suction pump
22: insertion part
24: operating part
26: universal cord
28*a*: air and water supply button
28*b*: suction button
29: angle knob
30: treatment tool insertion port
32*a*: connector
32*b*: connector
32*c*: connector
34*a*: air and water supply tube
34*b*: suction tube
36: ultrasound observation part

18

38: endoscope observation part
40: distal end part
41: exterior member
42: bending part
43: flexible part
44: treatment tool lead-out port
45: treatment tool channel
46: ultrasound transducer unit
47: laminate
48: ultrasound transducer
49: piezoelectric body
50: ultrasound transducer array
52: electrode
52*a*: individual electrode
52*b*: transducer ground
54: backing material layer
55: internal space
60: substrate
60*a*: side
60*b*: side
60*c*: side
62: electrode pad
63: first electrical bonded portion
64: ground electrode pad
76: acoustic matching layer
78: acoustic lens
80: filler layer
82: observation window
84: objective lens
86: solid-state imaging element
88: illumination window
90: cleaning nozzle
92: wiring cable
100: first cable
102: outer coat
104: second cable bundle
106: resin layer
108: second shield layer
110: first non-coaxial cable
112: signal wire
112*a*: conductor
112*b*: insulating layer
114: ground wire
116: first cable bundle
116*a*: distal end
118: first shield layer
130: fixing member
132: connecting member
134: insulation coating member
150: connector substrate
150*a*: side
152: connector electrode pad
153: fourth electrical bonded portion
160: relay substrate
160*a*: side
160*b*: side
160*c*: side
160*d*: side
162: first cable-side electrode pad
163: second electrical bonded portion
164: second cable-side electrode pad
165: third electrical bonded portion
170: second cable
172: outer coat
180: second non-coaxial cable
182: signal wire
184: ground wire

186: third cable bundle
188: second shield layer
190: second cable
192: coaxial cable
194: signal wire
196: outer coat
200: relay substrate
200*a*: first relay substrate
200*b*: second relay substrate
200*c*: substrate connector
200*d*: substrate connector
210: relay substrate
210*a*: first relay substrate
210*b*: second relay substrate
210*c*: third relay substrate
210*d*: substrate connector
210*e*: substrate connector
210*f*: substrate connector
210*g*: substrate connector

What is claimed is:

1. An ultrasound endoscope comprising:

an insertion part configured to be inserted into a subject;

a plurality of transducers which are arranged in a distal end of the insertion part, and configured to transmit and receive ultrasound;

a first cable whose distal end side is connected to the insertion part;

a substrate configured to electrically connect the plurality of transducers and the distal end side of the first cable;

a second cable which is disposed on a proximal end side from the first cable; and a relay substrate configured to electrically connect the proximal end side of the first cable and a distal end side of the second cable, wherein the first cable comprises:

a plurality of first non-coaxial cables; and an outer coat which coats the plurality of first non-coaxial cables, each of the plurality of first non-coaxial cables comprises:

a first cable bundle including signal wires and ground wires; and a first shield layer configured to coat the first cable bundle, the substrate includes first electrode pads respectively connected to the plurality of transducers, the first electrode pads and the signal wires of the first cable bundle are electrically connected to form first electrical bonded portions, the first electrical bonded portions are collectively disposed for each first cable bundle, the relay substrate includes second electrode pads corresponding to the signal wires included in each first cable bundle, the second electrode pads and the signal wires of each first cable bundle are connected to form second electrical bonded portions, the second electrical bonded portions are collectively disposed for each first cable bundle, and the relay substrate is disposed in the insertion part.

2. The ultrasound endoscope according to claim 1, wherein the second cable comprises:

a plurality of second non-coaxial cables; and an outer coat which coats the plurality of second non-coaxial cables, each of the plurality of second non-coaxial cables comprises: a third cable bundle including signal wires and ground wires; and a second shield layer configured to coat the third cable bundle, the relay substrate includes third electrode pads corresponding to the signal wires included in each third cable bundle of the second cable, the third electrode pads and the signal wires of each third cable bundle are connected to form third electrical bonded portions, the third electrical bonded portions are collectively disposed for each third cable bundle, and the relay substrate electrically connects the second electrical bonded portions and the third electrical bonded portions in different arrangement orders, in a one-to-one correspondence relationship.

3. The ultrasound endoscope according to claim 1, further comprising a connector substrate which is electrically connected to the proximal end side of the second cable and disposed in a connector which electrically connect the ultrasound endoscope with an ultrasound processor device configured to electrically process ultrasound signals from the plurality of transducers.

4. The ultrasound endoscope according to claim 3, wherein the connector substrate includes connector electrode pads corresponding to the signal wires included in each third cable bundle of the second cable, the connector electrode pads and the signal wires included in each third cable bundle are connected to form fourth electrical bonded portions, and the fourth electrical bonded portions are collectively disposed for each third cable bundle.

5. The ultrasound endoscope according to claim 1, wherein the second cable is configured by putting together a plurality of coaxial cables each having a signal wire.

6. The ultrasound endoscope according to claim 2, wherein the signal wires included in the second cable have a greater outside diameter, a longer outer peripheral length, or both a greater outside diameter and a longer outer peripheral length than the signal wires included in the first cables.

7. The ultrasound endoscope according to claim 1, further comprising at least one fixing member that reinforces the relay substrate.

8. The ultrasound endoscope according to claim 7, wherein the at least one fixing member is a metallic member, and the metallic member is electrically connected to the first shield layer of each of the plurality of first non-coaxial cables.

9. The ultrasound endoscope according to claim 1, further comprising an insulation coating member configured to coat the relay substrate.

10. The ultrasound endoscope according to claim 1, further comprising an illumination window which is disposed on the distal end side from the plurality of transducers, and through which illumination light for illuminating inside of the subject, is emitted.

* * * * *